US010441530B2

(12) United States Patent
Osborne et al.

(10) Patent No.: US 10,441,530 B2
(45) Date of Patent: Oct. 15, 2019

(54) SKIN PENETRATION ENHANCING SYSTEMS FOR POLAR DRUGS

(71) Applicant: AmDerma Pharmaceuticals, LLC, Bridgewater, NJ (US)

(72) Inventors: David W. Osborne, Fort Collins, CO (US); Pramod P. Sarpotdar, Huntington, CA (US); Arturo J. Angel, Santa Rosa, CA (US); Inigo Saenz de Tejada Gorman, Madrid (ES); Pedro Cuevas Sànchez, Madrid (ES)

(73) Assignee: AmDerma Pharmaceuticals, LLC, Bridgewater, NJ (US)

( * ) Notice: Subject to any disclaimer, the term of this patent is extended or adjusted under 35 U.S.C. 154(b) by 0 days.

(21) Appl. No.: 15/697,244

(22) Filed: Sep. 6, 2017

(65) Prior Publication Data
US 2018/0078495 A1  Mar. 22, 2018

Related U.S. Application Data

(63) Continuation of application No. 12/867,875, filed as application No. PCT/US2009/034304 on Feb. 17, 2009, now abandoned.

(60) Provisional application No. 61/029,231, filed on Feb. 15, 2008.

(51) Int. Cl.
*A61K 9/00* (2006.01)
*A61K 31/185* (2006.01)
*A61K 47/06* (2006.01)
*A61K 47/10* (2017.01)
*A61K 47/26* (2006.01)
*A61K 47/38* (2006.01)

(52) U.S. Cl.
CPC .......... *A61K 9/0014* (2013.01); *A61K 31/185* (2013.01); *A61K 47/06* (2013.01); *A61K 47/10* (2013.01); *A61K 47/26* (2013.01); *A61K 47/38* (2013.01)

(58) Field of Classification Search
CPC ...... A61K 31/185; A61K 47/06; A61K 47/10; A61K 47/26; A61K 47/38; A61K 9/0014
See application file for complete search history.

(56) References Cited

U.S. PATENT DOCUMENTS

| | | | |
|---|---|---|---|
| 2,550,622 A | 4/1951 | Taub | |
| 4,438,095 A * | 3/1984 | Grollier | A61K 8/03 424/70.13 |
| RE33,107 E * | 11/1989 | Dikstein | A61K 8/671 514/46 |
| 5,641,814 A | 6/1997 | Martin | |
| 7,252,816 B1 | 8/2007 | Angel et al. | |
| 7,968,531 B2 | 6/2011 | Cuevas Sanchez et al. | |
| 8,101,660 B2 | 1/2012 | Cuevas Sanchez et al. | |
| 2007/0149618 A1 | 6/2007 | Cuevas Sanchez et al. | |
| 2008/0113947 A1 | 5/2008 | Cuevas Sanchez et al. | |
| 2008/0113948 A1 | 5/2008 | Cuevas Sanchez et al. | |
| 2008/0114075 A1 | 5/2008 | Cuevas Sanchez et al. | |
| 2008/0125485 A1 | 5/2008 | Cuevas Sanchez et al. | |

FOREIGN PATENT DOCUMENTS

| | | | |
|---|---|---|---|
| EP | 1719509 A1 | 11/2006 | |
| WO | WO-2007029187 A2 * | 3/2007 | ............ A61K 8/416 |
| WO | 2008/020040 A2 | 8/2007 | |
| WO | 2007/099396 A2 | 9/2007 | |
| WO | 2008/020031 A1 | 2/2008 | |
| WO | 2008/020032 A1 | 2/2008 | |
| WO | 2008/020033 A1 | 2/2008 | |
| WO | 2008/020034 A1 | 2/2008 | |
| WO | 2008/020037 A1 | 2/2008 | |
| WO | 2008/020039 A2 | 2/2008 | |
| WO | 2008/020042 A1 | 2/2008 | |

OTHER PUBLICATIONS

Drugbank, Sodium Thiosulfate, Nov. 30, 2015, Canadian Institutes of Health, website accessed online at https://www.drugbank.ca/drugs/DB09499 (Year: 2015).*
"Handbook of Pharmaceutical Excipients", Pharmaceutical Press, 2006, 5th Ed., pp. 6-7, 83-85, 654-655.
PCT International Preliminary Report on Patentability in PCT/US2009/034304, dated Aug. 17, 2010, 9 pages.
PCT International Search Report in PCT/US2009/034304, dated May 15, 2009, 4 pages.
PCT International Written Opinion in PCT/US2009/034304, dated May 15, 2009, 8 pages.

* cited by examiner

*Primary Examiner* — Sarah Pihonak
(74) *Attorney, Agent, or Firm* — Servilla Whitney LLC

(57) ABSTRACT

The invention relates to pharmaceutical compositions and related methods for the topical administration of polar drugs. In a particular embodiment, the invention relates to a pharmaceutical composition comprising an active pharmaceutical agent that is a polar drug, such as potassium 2,5-dihydroxybenzenesulfonate, at least one occlusive agent, and at least one stabilizer.

7 Claims, 5 Drawing Sheets

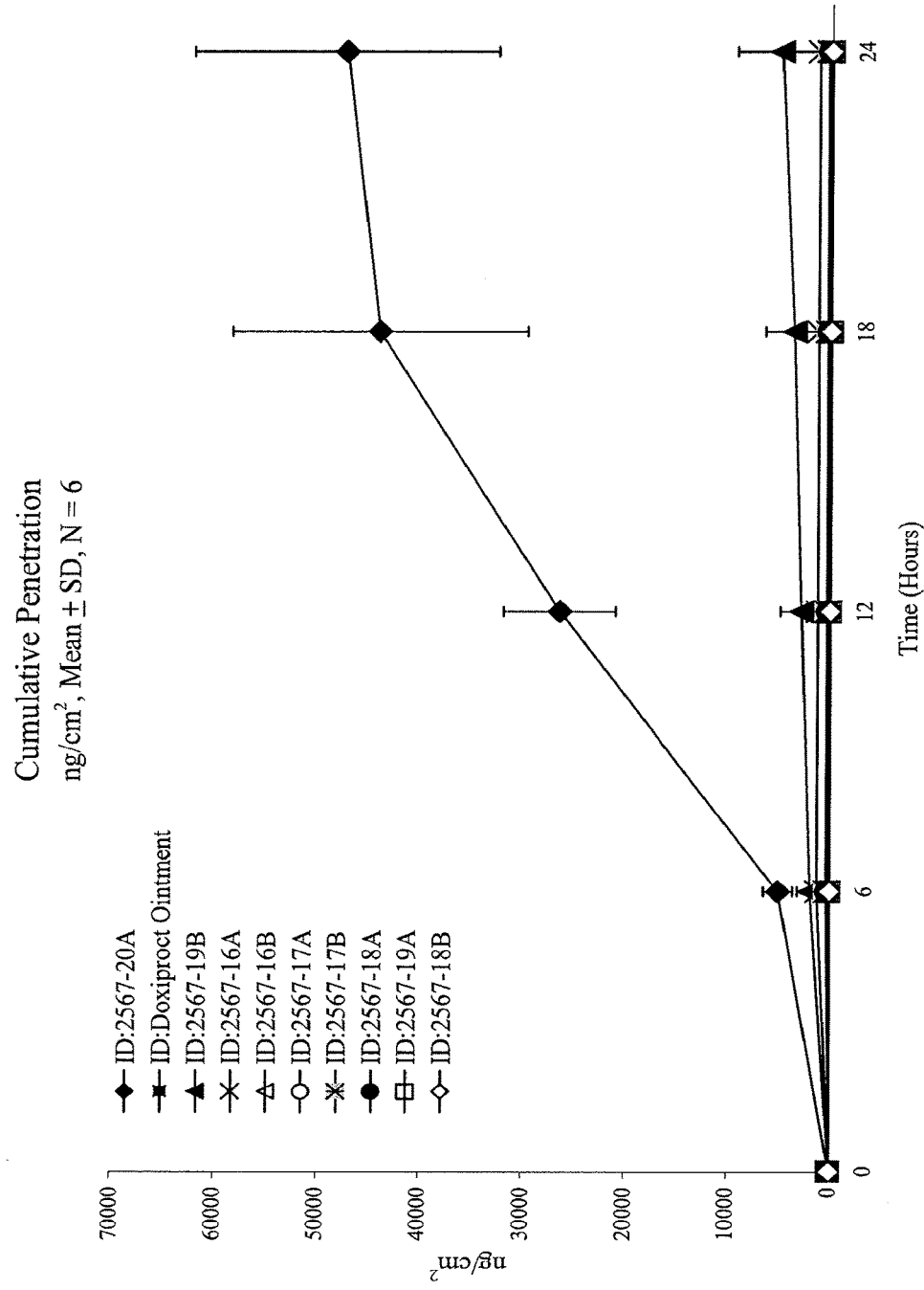
Figure 1. Cumulative Receptor Phase Levels of 2,5-dihydroxybenzenesulfonate in ng/cm$^2$

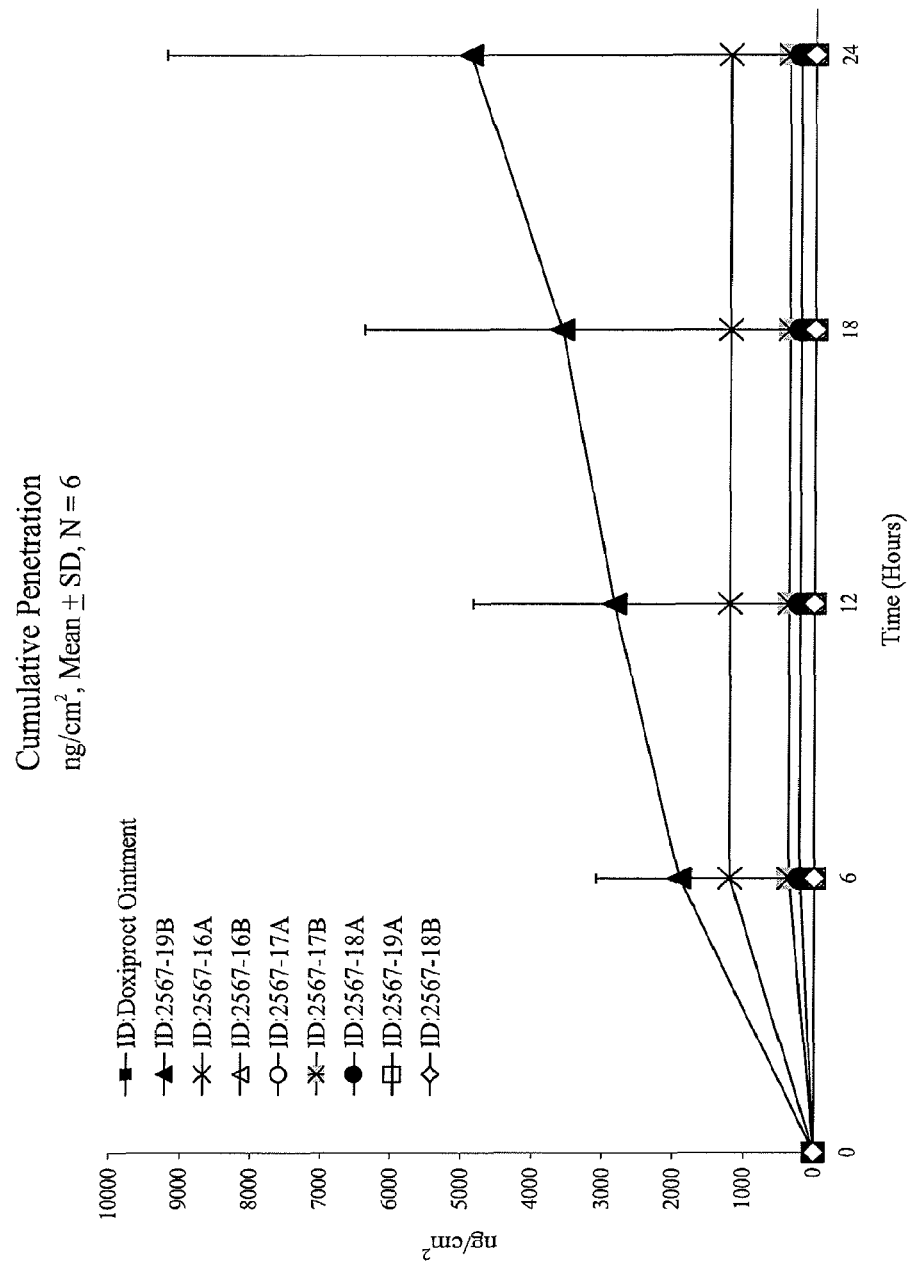
Figure 2. Cumulative Receptor Phase Levels of 2,5-dihydroxybenzenesulfonate in ng/cm$^2$ (without Control Formulation (10 % DMSO) 2567-20A)

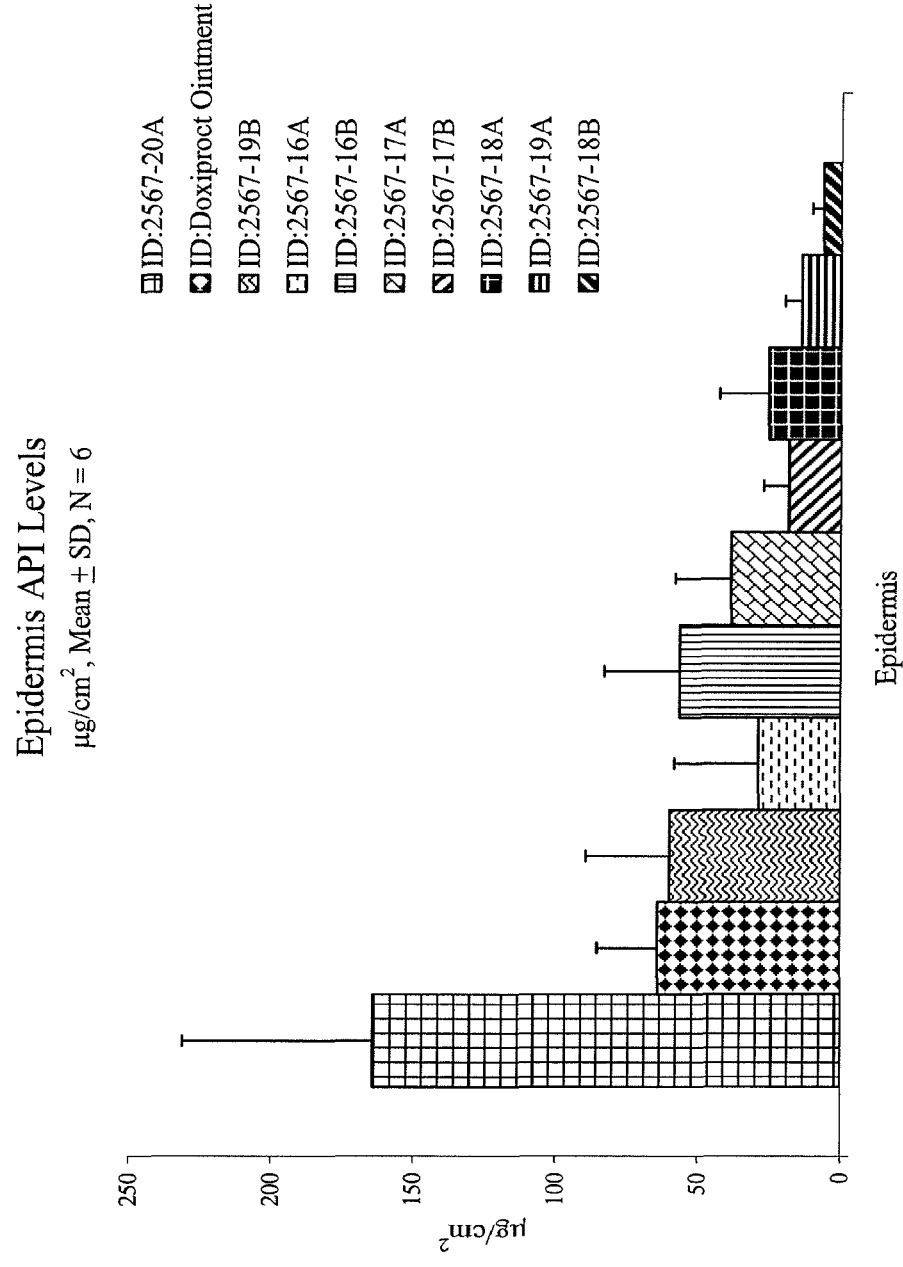
Figure 3. Epidermal Levels of 2,5-dihydroxybenzenesulfonate following 24 Hours of Topical Exposure in µg/cm$^2$

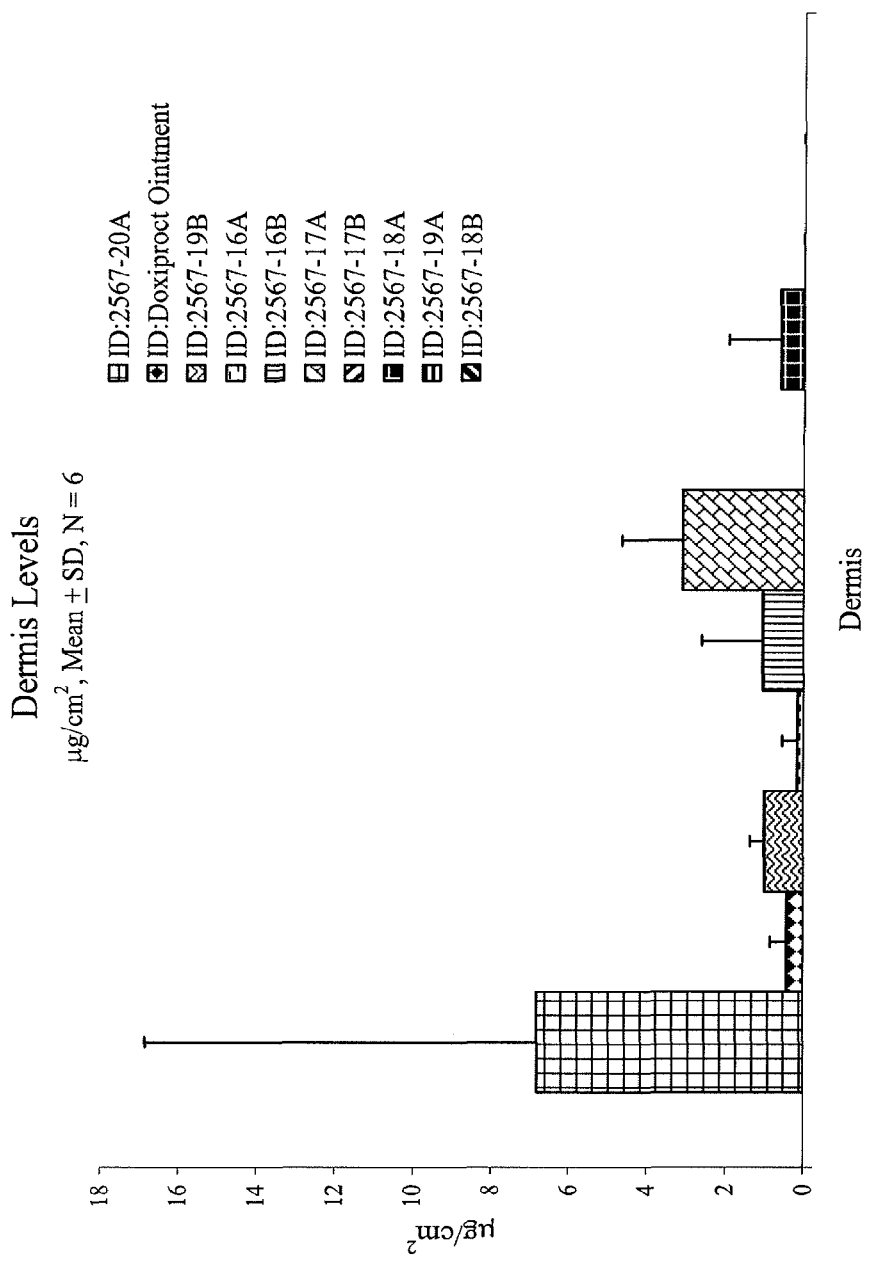
Figure 4. Dermal Levels of 2,5-dihydroxybenzenesulfonate following 24 Hours of Topical Exposure in μg/cm²

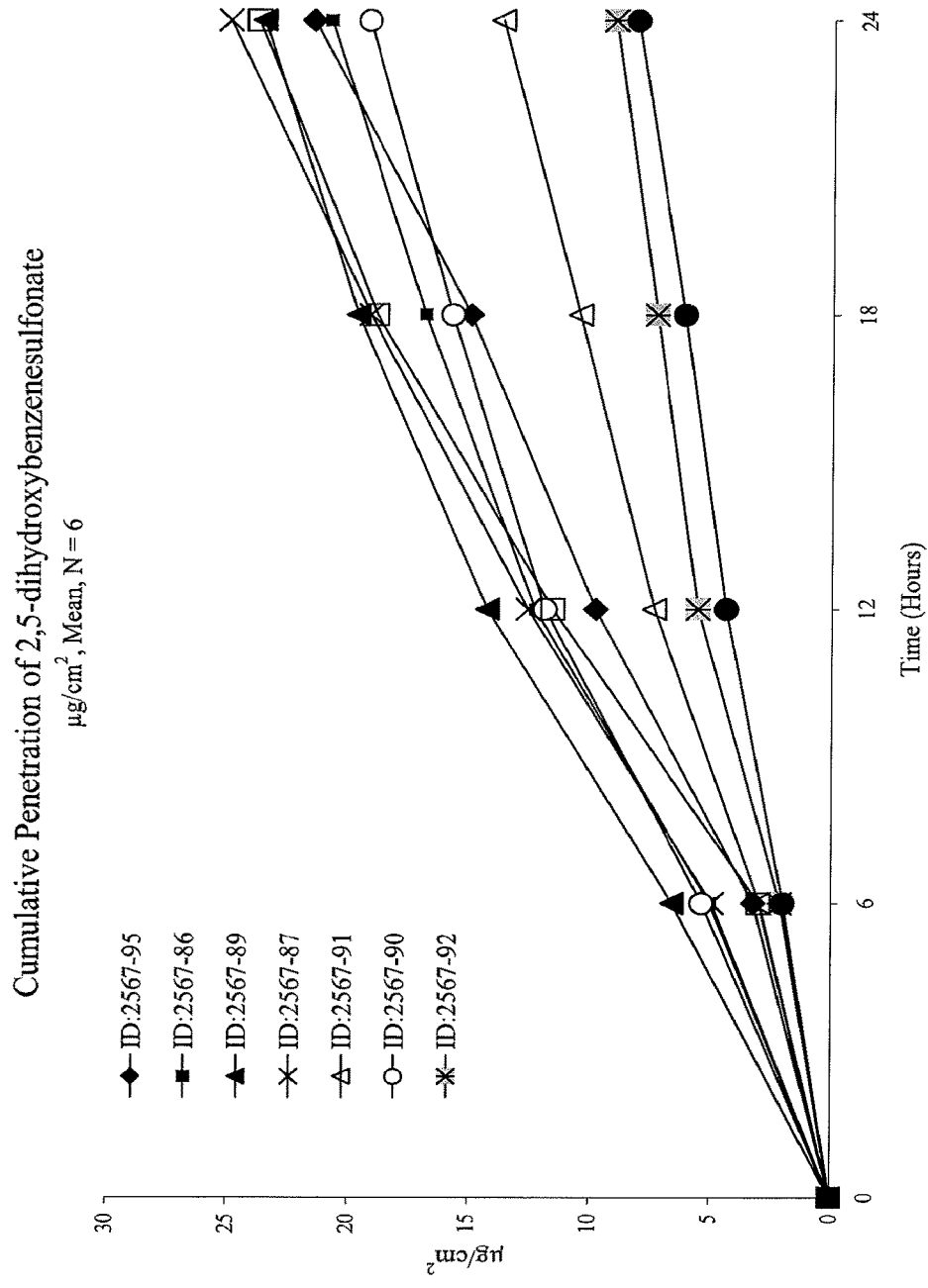
Figure 5. Cumulative Receptor Phase Levels of 2,5-dihydroxybenzenesulfonate in µg/cm²

SKIN PENETRATION ENHANCING SYSTEMS FOR POLAR DRUGS

CROSS-REFERENCE TO RELATED APPLICATIONS

This application is a continuation of and claims the benefit of priority of pending U.S. application Ser. No. 12/867,875, filed on Apr. 27, 2011, which is the National Stage entry of PCT/US2009/034304, filed on Feb. 17, 2009, which claims priority to U.S. Provisional Patent application No. 61/029,231, filed on Feb. 15, 2008. The foregoing applications, and all documents cited therein, are hereby incorporated herein by reference in their entireties.

BACKGROUND OF THE INVENTION

The composition of a formulation for topical application of a drug can play a vital role in the bioavailability and the efficacy of the drug on its targeted site of action. A key parameter for any drug product is its efficacy, which may require systemic uptake of the drug in an individual in order to be efficacious in the individual that is in need of treatment with the drug. Particularly in diseases of the skin, penetration into deep layers of the skin (e.g., the dermis and the deep layers of the epidermis) is important for the treatment of diseases located at these levels of the skin. Drugs that insufficiently penetrate the skin may be only partially effective in resolving such skin diseases, such as, for example, actinic keratosis, basal cell and squamous cell carcinomas, melanomas, psoriasis, atopic dermatitis, rosacea, hemangiomas, scars and queloids.

The stratum corneum provides the principal barrier to the percutaneous penetration of topically applied substances. It is the most superficial, cutaneous layer, the horny layer, which consists of flat, scalelike "squames" made up of the fibrous protein, keratin. The squames are continually being replaced from below by epidermal cells that die in the process of manufacturing keratin.

Topical administration of ionic or polar drugs therefore poses challenges in that the charged or ionizable nature of an ionic or polar drug typically acts as a barrier to penetration of the skin. This has been shown to be due, in part, to the nonpolar nature of the outer, horny layer of skin, such as the stratum corneum of human skin, which results in charged compounds typically encountering high resistance to permeation.

Though there is no one set way of formulating ionizable compounds, polar drugs are typically formulated for topical administration with penetration enhancers, excipients that are thought to alter the stratum corneum by denaturing proteins and lipid bilayer structures or by altering its pores via irritation or hydration. However, the amount of polar drug, for example, a pharmaceutically acceptable salt form of a drug, which is capable of penetrating skin from such topically applied formulations, is generally low.

SUMMARY OF THE INVENTION

In certain embodiments, the present invention relates to a topical pharmaceutical skin penetration enhancing system, comprising an active pharmaceutical agent, an occlusive agent; and a stabilizer, wherein the active pharmaceutical agent is polar or ionic and wherein at least 0.1% of the applied dose of the active pharmaceutical agent is capable of penetrating skin over a period of 24 hours. In other embodiments, at least 0.5%, at least 1.0%, at least 3.0%, or at least 5.0% of the applied dose of the active pharmaceutical agent is capable of penetrating skin over a period of 24 hours.

In some embodiments, the active pharmaceutical agent is in a salt form.

In further embodiments, a skin penetration enhancing system of the invention comprises a surfactant.

In yet other embodiments, a skin penetration enhancing system comprises one or more of an agent selected from the group consisting of: a stiffening agent, a preservative, an antioxidant, a pH adjuster, and a solvent.

In a particular embodiment, a skin penetration enhancing system comprises an active pharmaceutical agent that is a 2,5-dihydroxybenzene derivative represented by Formula (I) or a pharmaceutically acceptable salt, solvate, isomer, or prodrug thereof, wherein the compound of Formula (I) is:

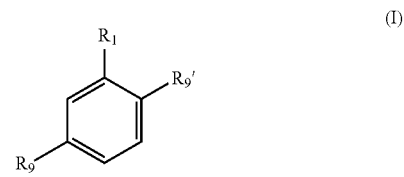

wherein:
$R_1$ is —$(CH_2)_aY$ or —CH=CH—$(CH_2)_pY$;
Y is —$SO_3H$, —$(SO_3)^-.X^+$, —$SO_3R_3$, —$PO_3H$, —$(PO_3)^-.X^+$, —$PO_3R_3$, —$CO_2H$, -$(CO_2)^-.X^+$ or —$CO_2R_3$;
$X^+$ is an organic cation or an inorganic cation, such that the general charge of the compound of Formula (I) is neutral;
$R_9$ and $R_{9'}$ are independently selected from —OH and —$OR_2$, wherein when $R_9$ and $R_{9'}$ are both —$OR_2$, then said $R_9$ and $R_{9'}$ can be the same or different;
$R_2$ is a substituted or unsubstituted alkyl group, a substituted or unsubstituted aryl group, a substituted or unsubstituted alkylsulfonyl group, a substituted or unsubstituted arylsulfonyl group, a substituted or unsubstituted alkylcarbonyl group or a substituted or unsubstituted arylcarbonyl group;
$R_3$ is a substituted or unsubstituted alkyl group or a substituted or unsubstituted aryl group;
a is a number selected from 0, 1, 2 , 3, 4, 5 and 6; and
p is a number selected from 0, 1, 2 , 3, 4, 5 and 6.

In certain embodiments, wherein the active pharmaceutical agent is selected from the group consisting of: calcium 2,5-dihydroxybenzenesulfonate (calcium dobesilate); potassium 2,5-dihydroxybenzenesulfonate (potassium dobesilate); magnesium 2,5-dihydroxybenzenesulfonate (magnesium dobesilate); and diethylamine 2,5-dihydroxybenzenesulfonate (ethamsylate). In a particular embodiment, the active pharmaceutical agent is potassium 2,5-dihydroxybenzenesulfonate (potassium dobesilate).

In certain embodiments, the invention relates to a topical pharmaceutical composition comprising potassium 2,5-dihydroxybenzenesulfonate (potassium dobesilate), wherein when the pharmaceutical composition is applied to skin in a Bronaugh flow-through diffusion cell system at a dose of about 5 mg/cm² of the composition, and the cells are maintained at a constant temperature of about 32° C., the receptor phase is phosphate buffered saline comprising 0.1% sodium azide and 4% bovine serum albumin; and the receptor phase flow-through is about 1 to 2 mL per hour, the in vitro tissue permeation of the potassium 2,5-dihydroxybenzenesulfonate ranges from about 1.0% to about 10% of the applied dose within 24 hours of application. In other embodiments, the in vitro tissue permeation of the potassium 2,5-dihydroxybenzenesulfonate ranges from about 0.5% to about 5% within 12 hours of application. In yet other embodiments, the in vitro tissue permeation of the potassium 2,5-dihydroxybenzenesulfonate ranges from about 0.2% to about 2.0% within 6 hours of application.

In certain embodiments, the occlusive agent in a skin penetration enhancing system of the invention is selected from the group consisting of: hydrocarbon waxes and oils. In some embodiments, a skin penetration enhancing system comprises at least two occlusive agents wherein the at least two occlusive agents are white petrolatum and mineral oil.

In some embodiments, a skin penetration enhancing system of the invention comprises a stabilizer, wherein the stabilizer is a surfactant selected from the group consisting of: emulsifying agents, cleansing agents, foam boosters, solubilizing agents, suspending agents, and hydrotropes. In certain embodiments, the stabilizer is an emulsifying agent selected from the group consisting of: steareth, sorbitan, polysorbate, and polyethylene glycol derivatives. In yet other embodiments, a skin penetration enhancing system comprises at least two emulsifying agents, wherein the at least two emulsifying agents are steareth-2 (Brij 72) and steareth-21 (Brij 721).

In certain embodiments, the invention relates to a topical pharmaceutical skin penetration enhancing system, comprising potassium 2,5-dihydroxybenzenesulfonate (potassium dobesilate); about 0.1-99% of at least one occlusive agent; and about 0.1-5% of at least one surfactant. In further embodiments, the skin penetration enhancing system comprises a preservative, an antioxidant, a pH adjuster, and a solvent. In yet other embodiments, the skin penetration enhancing system comprises about 0.1-20.0% potassium 2,5-dihydroxybenzenesulfonate , about 0.1-90.0% white petrolatum, about 0.1-90.0% mineral oil, about 0.1-50% stearyl alcohol, about 0.05-50% cetyl alcohol, about 0.1-5% steareth-2 (Brij 72), and about 0.1-5% steareth-21 (Brij 721). In further embodiments, the skin penetration enhancing system comprises about 0.1-5% benzyl alcohol, about 0.001-0.5% sodium thiosulfate pentahydrate, about 0.01-10% acetic acid, about 0.001-1.0% sodium acetate, and about 0-90.0% water.

In a particular embodiment, a skin penetration enhancing system of the invention comprises about 10% potassium 2,5-dihydroxybenzenesulfonate , about 20% white petrolatum, about 20% mineral oil, about 2.5% stearyl alcohol, about 0.5% cetyl alcohol, about 1.0% steareth-2, about 4.0% steareth-21, about 0.5% benzyl alcohol, about 0.1% sodium thiosulfate pentahydrate, about 0.05% acetic acid, about 0.02% sodium acetate, and water to 100%.

In some embodiments, the invention relates to a method of treating a skin disorder, comprising topically administering a skin penetration enhancing system as described herein to the effected area of a patient.

BRIEF DESCRIPTION OF THE DRAWINGS

FIG. 1 is a graph depicting cumulative receptor phase levels of 2,5-dihydroxybenzenesulfonate in ng/cm$^2$.

FIG. 2 is a graph depicting cumulative receptor phase levels of 2,5-dihydroxybenzenesulfonate in ng/cm$^2$ without control formulation (10% DMSO).

FIG. 3 is a graph depicting epidermal levels of 2,5-dihydroxybenzenesulfonate following 24 hours of topical exposure in µg/cm$^2$.

FIG. 4 is a graph depicting dermal levels of 2,5-dihydroxybenzenesulfonate following 24 hours of topical exposure in µg/cm$^2$.

FIG. 5 is a graph depicting cumulative receptor phase levels of 2,5-dihydroxybenzenesulfonate in µg/cm$^2$.

DETAILED DESCRIPTION OF THE INVENTION

Described herein are methods and compositions for the preparation of skin penetration enhancing systems for the topical administration of polar or ionic drugs.

The term "skin penetration enhancing system" refers to a composition comprising at least one active pharmaceutical agent, at least one occlusive agent, and at least one stabilizing agent. The active pharmaceutical agent is typically a polar drug, such as potassium 2,5-dihydroxybenzenesulfonate. A skin penetration enhancing system as described herein will typically enable transdermal penetration of at least 0.1%, at least 0.5%, at least 1.0%, at least 2.0%, at least 3.0%, at least 4.0%, or at least 5.0% of the applied dose of the active pharmaceutical agent.

The terms "active pharmaceutical agent", "active pharmaceutical ingredient", and "drug" are used interchangeably herein.

A polar drug is an electrically asymmetric molecule and may be used as an active pharmaceutical ingredient in a formulation of the invention. Often, a polar drug is water-soluble and ionizes in solution in distilled water at 25° C.

An "occlusive agent" refers to an excipient that provides occlusive properties to a formulation of the invention. Examples of occlusive agents include, but are not limited to, hydrocarbon bases such as white petrolatum, anhydrous absorption bases such as hydrophilic petrolatum, and anhydrous lanolin. Additional examples include water-in-oil emulsion bases such as lanolin and cold cream.

A "stabilizing agent" refers to an excipient that confers a stabilizing effect to a formulation of the invention, in particular, by preventing or aiding in the prevention of separation or degradation of a formulation of the invention into, for example, separate aqueous and oil phases. For example, a stabilizer, such as a surfactant that is an emulsifying agent, will generally prevent separation of the oil and water phases that may be present or may develop in a formulation of the invention over time. Generally, a stabilizer will prevent separation or degradation of a formulation of the invention after a period of at least one day, at least one week, at least one month, at least six months, or at least one year after manufacture when stored at 15° C. to 30° C. Storage may be at, for example, 22° C. A stabilizing agent may also be useful to maintain the chemical integrity of an active pharmaceutical ingredient. For example, a stabilizing agent, such as sodium thiosulfate, in a formulation of the invention may be useful to reduce the oxidation potential of the active ingredient in the formulation, such as 2,5-dihydroxybenzene sulfonate and of its related substances, e.g., hydroquinone.

The term "bioavailability" as used herein refers to the physiological availability of a given amount of a drug. The term may also refer to the proportion of the administered dose which is absorbed into the bloodstream.

The term "topical" refers to the administration of a compound by applying it on the body surface and includes, but is not limited to, transdermal administration and administration through the mucosa.

In certain embodiments, a formulation of the invention enhances penetration of an active agent into one or more layers of the skin. For example, in some embodiments, a formulation of the invention enhances penetration of an active agent into the epidermis. In other embodiments, a formulation of the invention enhances penetration of an active agent into the dermis. In yet other embodiments, a formulation of the invention enhances transdermal penetration of an active agent.

The term "transdermal" refers to the delivery of a compound that enters into the bloodstream through the skin.

The expression "through the mucosa" or "transmucosal" refers to the delivery of a compound that enters into the bloodstream through the mucosal tissue.

It has surprisingly been found by the inventors that transdermal penetration of a polar drug, such as for example, a salt, such as the potassium salt of 2,5-dihydroxybenzene sulfonic acid, can be enhanced by inclusion of the drug in a formulation comprising at least one occlusive agent and at least one stabilizing agent, wherein greater than 0.1% of the applied dose of the polar drug penetrates the dermis of the skin to which it is topically applied. In other embodiments, at least 0.1%, at least 0.5%, at least 1.0%, at least 2.0%, at least 3.0%, at least 4.0%, or at least 5.0% of the applied dose of a polar drug in a formulation of the invention penetrates the skin after application of the formulation to the skin.

In certain embodiments, at least 0.1%, at least 0.5%, at least 1.0%, at least 2.0%, at least 3.0%, at least 4.0%, or at least 5.0% of the applied dose of a polar drug in a formulation of the invention penetrates the skin within 24 hours of application of the formulation to the skin. In some embodiments, at least 0.01%, at least 0.05%, at least 0.1%, at least 1.0%, at least 2.0% of a polar drug in a formulation of the invention penetrates the skin within 18 hours of application. In other embodiments, 0.001%, at least 0.005%, at least 0.01%, at least 0.1%, at least 0.5%, at least 1.0% of a polar drug in a formulation of the invention penetrates the skin within 12 hours of application. In yet other embodiments, at least 0.0001%, at least 0.001%, at least 0.005%, at least 0.01%, at least 0.1%, at least 0.5% of a polar drug in a formulation of the invention penetrates the skin within 6 hours of application.

The inventors have surprisingly discovered that the transdermal penetration of the potassium salt of 2,5-dihydroxybenzene sulfonic acid, for example, is significantly enhanced in comparison to the calcium salt. In some embodiments, this uptake is statistically significant at both 6 hour and 12 hour time points after topical application to skin, for example, in an in vitro skin permeation test. Though calcium dobesilate has been commercially available in a topical formulation in, for example, Europe, a topical formulation capable of enhancing the transdermal penetration of dobesilate would be useful since, as described herein, certain commercial formulations do not enable transdermal uptake of the active ingredient, 2,5-dihydroxybenzene sulfonate. For example, commercial products containing calcium dobesilate, such as Doxiproct® and Doxivenyl Gel® (OM Pharma, Geneva, Switzerland) are primarily water based products, which lack an occlusive agent, in contrast to the inventive formulations described herein.

Accordingly, in particular embodiments, the skin penetration enhancing systems of the invention enhance the uptake of polar drugs that are salts. In certain embodiments, the inventive formulations described herein enhance the uptake of ionizable or non-ionizable small molecule drugs in salt form that are mono-valent salts. In a particular embodiment, a formulation of the invention comprises the potassium salt of 2,5-dihydroxybenzene sulfonic acid.

Enhanced permeability of polar drugs, such as the potassium and calcium salts of dobesilate, can be achieved with the inventive formulations disclosed herein. Without being bound to theory, it is thought that the enhanced permeation enabled by a skin penetration enhancing system of the invention may be due in part to skin occlusion provided by an occlusive agent at the site of application of a formulation of the invention and the respective thermodynamic activity of the one or more active pharmaceutical agents in the formulation (e.g., the degree of saturation of each compound in the formulation). For example, the thermodynamic activity of a potassium salt of 2,5-dihydroxybenzene sulfonic acid is likely greater than that of the calcium salt as its solubility in a water base vehicle is respectively lower and, therefore, at a higher thermodynamic potential when formulated at the same concentration. In addition, steric size of resulting salt moieties of a drug in a formulation of the invention may contribute to enhanced skin penetration of one pharmaceutically acceptable salt form of a drug relative to another. For example, potassium is a mono-valent metal and calcium is a di-valent metal. Typically, one potassium molecule will bind one dobesilate (2,5-dihydroxybenzene sulfonic acid) molecule and two molecules of dobesilate may bind to calcium.

In a further embodiment, the active pharmaceutical agent in a skin penetration enhancing system of the invention is a compound of Formula (I) or a pharmaceutically acceptable salt or solvate, isomer or prodrug thereof, wherein the compound of Formula (I) is:

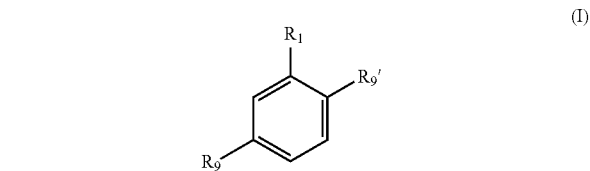

wherein:
$R_1$ is —$(CH_2)aY$ or —$CH$=$CH$—$(CH_2)pY$;
Y is —$SO_3H$, —$SO_3$—.$X+$, —$SO_3R_3$, —$PO_3H$, —$PO_3$—.$X+$, —$PO_3R_3$, —$CO_2H$, —$CO_2$—.$X+$ or —$CO_2R_3$;

$X+$ is an organic cation or an inorganic cation, such that the general charge of the compound of Formula (I) is neutral;

$R_9$ and $R_{9'}$ are independently selected from —OH and —$OR_2$; wherein when $R_9$ and $R_{9'}$ are both —$OR_2$, then said $R_9$ and $R_{9'}$ can be the same or different;

$R_2$ is a substituted or unsubstituted alkyl group, a substituted or unsubstituted aryl group, a substituted or unsubstituted arylalkyl group, a substituted or unsubstituted alkylsulfonyl group, a substituted or unsubstituted arylsulfonyl group, a substituted or unsubstituted alkylarylsulfonyl group, a substituted or unsubstituted arylalkysulfonyl group, a substituted or unsubstituted aryloxyalkyl group, a substituted or unsubstituted alkylcarbonyl group or an arylcarbonyl group, a carboxyl group, a substituted or unsubstituted alkoxycarbonyl group, a substituted or unsubstituted carboxyalkyl group, in particular —$CH_2$—COOH, or a substituted or unsubstituted alkoxy- aryloxy- arylalkoxy- or alkylaryloxy-carbonylalkyl, in particular —$CH_2$-$COOR_3$;

$R_3$ is a substituted or unsubstituted alkyl group, a substituted or unsubstituted aryl group, a substituted or unsubstituted arylalkyl group, or a substituted or unsubstituted alkylaryl group;

a is number selected from 0, 1, 2, 3, 4, 5 and 6; and
p is number selected from 0, 1, 2, 3, 4, 5 and 6.

"Alkyl" refers to a linear or branched chain hydrocarbon radical comprising carbon atoms and hydrogen, with no unsaturations, with one to twelve, preferably one to eight, more preferably one to six carbon atoms, bound to the rest of the molecule by a single bond, for example, methyl, ethyl, n-propyl, i-propyl, n-butyl, t-butyl, n-pentyl, etc.

"Alkenyl" refers to a linear or branched chain hydrocarbon radical comprising carbon atoms and hydrogen atoms, containing at least one unsaturation, with two to twelve, preferably two to eight, more preferably two to six carbon atoms, bound to the rest of the molecule by a single bond.

"Cycloalkyl" refers to a saturated carbocyclic ring having between three and eight, preferably three to six carbon atoms. They may exhibit a bridged structure. Suitable cycloalkyl groups include, but are not limited to, cycloalkyl groups such as cyclopropyl, cyclobutyl, cyclopentyl or cyclohexyl.

"Alkynyl" refers to a linear or branched chain hydrocarbon radical comprising carbon atoms and hydrogen, containing at least one triple carbon-carbon bond, whether conjugated or not, with two to twelve, preferably two to eight, more preferably two to six carbon atoms, bound to the rest of the molecule by a single bond such as —CCH, —CH$_2$CCH, —CCCH$_3$, —CH$_2$CCCH$_3$.

"Aryl" refers to an aromatic hydrocabon radical containing from six to ten carbon atoms such as phenyl or naphthyl. "Aralkyl" refers to an aryl group bound to the rest of the molecule by an alkyl group such as benzyl and phenetyl.

"Heterocycle" refers to a stable 3 to 15-membered ring comprised of carbon atoms and between one and five heteroatoms selected from the group consisting of nitrogen, oxygen and sulfur, preferably a 4 to 8-membered ring with two, three or four heteroatoms, more preferably a 5 or 6-membered ring with one, two or three heteroatoms. The heterocycle may be a monocyclic, bicyclic or tryciclic ring system that may include fused ring systems; bridged structures; and the nitrogen, carbon or sulfur atoms in the heterocyclic radical may be optionally oxidized; the nitrogen atom may be optionally quaternized; and the heterocyclic radical may be partially or completely saturated or it may be aromatic. Examples of such heterocycles include, but are not limited to, azepines, benzimidazole, benzothiazole, furan, isothiazole, imidazole, indole, piperidine, piperazine, quinoline, thiadiazol, tetrahydrofuran.

Unless otherwise specified, the alkyl, cycloalkyl, alkenyl, alkynyl, aryl, aralkyl and heterocycle radicals may be optionally substituted by one, two or three substituents such as halo, alkyl, alkenyl, alkynyl, aryl, cycloalkyl, hydroxy, alkoxy, sulfoxy, O-Benzyl, O-Benzoyl, carboxyl, alkylcarboxyl, arylcarboxyl, alkylcarbonyl, arylcarbonyl, cyano, carbonyl, acyl, alkoxycarbonyl, amino, alkylamino, dialkylamino, arylamino, diarylamino, alkylarylamino, imino, alkylsulphinyl, amidyl, carbamoyl, sulfonamido, nitro, nitrite, nitrate, thionitrate and carboxamido.

The term "alkoxycarbonyl" refers to a compound having the formula —C(=O)O—, where the C-terminal is bound to the molecule and the O-terminal is bound to a carbon atom to form an ester function. Said carbon atom may be part of an alkyl, alkenyl, cycloalkyl, alkynyl, aryl, aralkyl or heterocyclic group.

The term "alkoxycarbonylalkyl" refers to a compound of the previously defined formula —C(=O)O—, wherein the C-terminal binds to a molecule through an alkyl group. The terms "aryloxy- arylalkoxy- or alkylaryloxy-carbonylalkyl" will be understood similarly to "alkoxycarbonylalkyl".

The term "arylalkyl" refers to an aryl radical, as defined herein, bound to an alkyl radical, as defined herein. The exemplary arylalkyl groups include benzyl, phenylethyl, 4-hydroxybenzyl, 3-fluorobenzyl, 2-fluorophenylethyl and the like.

The term "alkylaryl" refers to an alkyl group, as defined herein, to which an aryl group is bound, as defined herein. Exemplary alkylaryl groups include benzyl, phenylethyl, hydroxybenzyl, fluorobenzyl, fluorophenylethyl, and the like.

The term "alkylsulfonyl" refers to a $R_{50}$-S(O)$_2$—, wherein $R_{50}$ is a lower alkyl group, as defined herein.

The term "arylsulfonyl" refers to a $R_{55}$-S(O)$_2$—, wherein $R_{55}$ is an aryl group, as defined herein.

The term "alkylsulphinyl" refers to a $R_{55}$-S(O)$_2$—, wherein $R_{55}$ is an aryl group, as defined herein.

The term "arylsulphinyl" refers to a $R_{55}$-S(O)$_2$—, wherein $R_{55}$ is an aryl group, as defined herein.

The term "sulfonamide" refers to a —S(O)$_2$—N($R_{51}$)($R_{57}$), wherein $R_{51}$ and $R_{57}$ are each independently a hydrogen atom, an alkyl group, an aryl group, heterocycle, as defined herein, or else $R_{51}$ and $R_{57}$ together form a heterocyclic ring, a cycloalkyl group or a bridged cycloalkyl group, as defined herein.

The term "alkylsulfonamide" refers to a sulfonamide group, as defined herein, bound to an alkyl group, as defined herein.

The term "arylsulfonamide" refers to a sulfonamide group, as defined herein, bound to an aryl group, as defined herein.

The term "alkylcarbonyl" refers to a $R_{52}$-C(O)$_2$—, wherein $R_{52}$ is an alkyl group, as defined herein.

The term "arylcarbonyl" refers to the $R_{55}$-S(O)$_2$— radical, wherein R55 is an aryl group, as defined herein.

The term "carboxamide" refers to a —C(O)N($R_{52}$)($R_{58}$) radical, wherein $R_{52}$ and $R_{58}$ are each independently a hydrogen atom, an alkyl group, an aryl group or an heterocyclic group, as defined herein or else $R_{51}$ and $R_{57}$ together form an heterocyclic ring, a cycloalkyl group, or a bridged cycloalkyl group, as defined herein.

The term "carboxylic ester" refers to —C(O)0$R_{59}$, wherein $R_{59}$ is an alkyl group an aryl group or an heterocyclic group, as defined herein.

The term "alcoxyalkyl" refers to an alcoxy group, as defined herein, bound to an alkyl group, as defined herein. Examples of alcoxyalkyl groups are methoxymethyl, methoxyethyl, isopropoximethyl and the like.

The term "amine" refers to any organic compound containing at least one basic nitrogen atom.

The term "organic cation" refers to a positively charged organic ion. Exemplary organic cations include ammonium cations unsubstituted or substituted with alkyl, primary, secondary or tertiary amines, alkylamines, arylamines, cyclic amines, N,N'-dibenzylethylenediamine, and the like.

The term "inorganic cation" refers to a positively charged metal ion. Exemplary inorganic cations include Group I metal cations such as sodium, potassium, magnesium, calcium and the like.

The term "prodrug" refers to compounds that rapidly convert in vivo into pharmacologically active compounds. Prodrug design is generally studied in Hardma et al. (eds.), Goodman and Gilman's The Pharmacological Basis of Therapeutics, 9th ed., pages 11-16 (1996). A thorough study is presented in Higuchi et al., Prodrugs as Novel Delivery Systems, vol. 14, ASCD Symposium Series, and in Roche (ed.), Bioreversible Carriers in Drug Design, American Pharmaceutical Association and Pergamon Press (1987).

An active pharmaceutical agent in a formulation of the invention having one or more asymmetric carbon atoms may exist as optically pure enantiomers, pure diastereomers, mixtures of enantiomers, mixtures of diastereomers, racemic mixtures of enantiomers, diastereomeric racemates or mixtures of diastereomeric racemates.

An "ester derivative of a compound of formula (I)" refers to the compound of formula (I) wherein at least one of $R_9$ and $R_{9'}$ is an ester group. For example, the ester derivative of 2,5-dihydroxybezene sulfonic acid or dobesilate ester derivative refers to the compound 2,5-dihydroxybezene sulfonic acid (dobesilate) wherein at least one of the hydroxyl groups has been esterified.

An "ester of a compound of formula (I)" refers to an ester of the sulfonic or carboxylic acid group at position 1. For example, the ester of 2,5-dihydroxybenzensulfonic acid or ester of dobesilate refers to an ester of the sulfonic acid group at position 1.

The X+ cation in the compound of Formula (I) may be any physiologically acceptable cation known in the art, that includes but is not limited to those described in P. Heinrich Stahl, Camille G. Wermuth (eds.), "Handbook of Pharmaceutical Salts Properties, Selections and Use", Verlag Helvetica Chimica Acta, Zurich, Switzerland, Wiley-VCH, Weinheim, Germany, 2002.

The X+ cation is typically selected in such a way that the general charge of Formula (I) is neutral.

In certain embodiments of the invention, the inorganic cation is sodium, potassium, lithium, calcium, or magnesium.

In another embodiment of the invention, the organic cation is [NH4-pRp]+: wherein p is an integer between 0 and 4 and R is an alkyl group having one to six carbon atoms such as, for example, methyl, ethyl, n-propyl, i-propyl, t-butyl or n-pentyl.

In yet another embodiment of the invention, the organic cation is the diethylamine [H2N+(C2H5)2], piperazine or pyridine group.

In certain embodiments, the active pharmaceutical agent is selected from the group consisting of potassium 2,5-dihydroxybenzenesulfonate (potassium dobesilate), calcium 2,5-dihydroxybenzenesulfonate (calcium dobesilate), magnesium 2,5-dihydroxybenzenesulfonate (magnesium dobesilate), and diethylamine 2,5-dihydroxybenzenesulfonate (ethamsylate).

Potassium 2,5-dihydroxybenzenesulfonate is synonymous with potassium hydroquinone monosulfonate, potassium hydroquinonesulfonate, and potassium dobesilate. The terms may be used interchangeably herein and refer to a compound of Formula (I), wherein the compound of Formula (I) is:

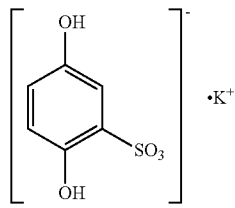

Other examples of polar drugs that may be suitable for use in the skin penetration enhancing systems described herein include polar anti-inflammatory or antirheumatic agents, for example ibuprofen; antibacterial agents, for example agents that may be useful in the treatment of acne (for example, clindomycin sodium phosphate, or tetracycline); a hormone, for example an estrogen; a polar analgesic, for example fentanyl; a polar motion-sickness treatment molecule, for example scopolamine or hyoscine; an antihypertensive, for example clonidine; a vasodilator or coronary vasodilator, for example nitroglycerine; or nicotine.

Further examples of suitable polar drugs include a polar corticosteroid formulation, for example a salt of an esterified corticosteroid, for example a salt of a phosphate or succinate ester. In these embodiments, the polar corticosteroid formulation may be soluble in water and will typically be in a form commonly used for injections or solutions. Suitable salts of esters of corticosteroids include betamethasone sodium phosphate, dexamethasone sodium phosphate, hydrocortisone sodium phosphate, hydrocortisone sodium succinate, methylprednisolone sodium succinate and prednisolone sodium succinate.

A drug formulated in a skin penetration enhancing system according to the invention may be useful in treating a skin disease and/or may be a drug that is useful when administered transdermally. The drug, for example, potassium 2,5-dihydroxybenzenesulfonate, may constitute from 0.001 to 30% w/w, from 1 to 20% w/w, from 5 to 10% w/w of the composition, for example, an emulsion.

It will be appreciated that it is advantageous that the above proportions are present in a composition of the invention that is a formulation, for example an emulsion, as may be administered to a patient, for example applied to the skin of the patient. It will further be appreciated that a composition of the invention may be useful in preparing a formulation, for example an emulsion, suitable for administration to a patient, for example application to the skin of a patient; for example, the composition may form the aqueous phase of the emulsion, or it may be a concentrate used in the preparation of the aqueous phase of the emulsion, as known to those skilled in the art.

It will be appreciated that a formulation of the invention may comprise more than one polar drug. Thus, for example, a composition, such as an emulsion, of the invention may comprise a 2,5-dihydroxybenzene derivative, such as potassium 2,5-dihydroxybenzene sulfonate, and a polar antibiotic. The antibiotic may constitute 0.01 to 10% w/w, for example, from about 0.25 or 0.5% w/w of the composition, for example, an emulsion or other formulation as administered to a patient.

In yet other embodiments, a formulation of the invention comprises at least one polar drug and at least one non-polar drug. In certain embodiments, a non-polar drug is applied to the skin before, after, or at the same time as a formulation of the invention.

In further embodiments, a formulation of the invention comprises one or more stabilizers, such as one or more surfactants, which serve to stabilize the formulation. The inventors have surprisingly found that addition of one or more stabilizers to a formulation of the invention comprising a polar drug, such as a salt, such as potassium 2,5-dihydroxybenzenesulfonate, does not negatively impact the ability of the formulation to enhance the transdermal penetration of the drug.

In some embodiments, a stabilizer may also function as an occlusive agent in a formulation of the invention.

In further embodiments, the occlusive agent and/or stabilizer may function to enhance penetration of the active pharmaceutical agent into one or more layers of the skin. For example, the occlusive agent and/or stabilizer may enhance one or more of epidermal, dermal, or transdermal penetration of a polar drug.

The expression "penetration enhancer" refers to an agent capable of increasing the permeability of the skin or mucosal tissue to a pharmacologically active compound. Typically, a penetration enhancer is selected in such a way that it increases the penetration rate through the skin or mucosal tissue.

Penetration enhancers enhance percutaneous delivery of an active pharmaceutical agent into the skin or mucosal tissue, typically providing transdermal or transmucosal transmission of the active pharmaceutical agent. In the case of some enhancers, the amount and rate of transmission and thus the difference between providing transdermal or transmucosal delivery and not doing so will lie in the selection of the amount of enhancer used, the intactness of the skin, the type of skin or mucosal tissue that is being treated, the nature of the active pharmaceutical agent, and the like. These parameters can be optimized for a particular condition by one of ordinary skill in the art.

Thus, suitable topical penetration enhancing agents can be selected for a particular use by those skilled in the art, for example, with reference to one of many standard texts in the art, such as Remington's The Science and Practice of Pharmacy, 21st Edition, Lippincott Williams & Wilkins, Philadelphia, Pa. (2006), in particular Chapter 44. For example, suitable enhancers for transdermal absorption include ethanol, propylene glycol, water, sodium oleate, leucinic acid, oleic acid, capric acid, sodium caprate, lauric acid, sodium laurate, neodecanoic acid, dodecyl-amine, cetryl lactate, myristyl lactate, lauryl lactate, methyl laurate, phenyl ethanol, hexamethylene lauramide, urea and derivatives, dodecyl N, N-dimethylamino acetate, hydroxyethyl lactamide, phyophatidylcholine, sefsol-318 (a medium chain glyceride), isopropyl myristate, isopropyl palmitate, several surfactants, including polyoxyethylene (10) lauryl ether (Brij 361 R), diethyleneglycol lauryl ether (PEG-2-L), laurocapram (Azone; 1,1-dodecylazacycloheptan-2-one), acetonitrile, 1-decanol, 2-pyrrolidone, N-methylpyrrolidone, N-ethyl-1-pyrrolidone, 1-Methyl-2-pyrrolidone, 1-lauryl-2-pyrrolidone, sucrose monooleate, dimethylsulfoxide (DMSO), decylmethylsulfoxide (n) enhances primarily polar or ionic molecules (soluble in ethanol), acetone, polyethylene glycol 100-400 MW, dimethylacetamide, dimethylforamide, dimethylisosorbide, sodium bicarbonate, various $N_{7-16}$-alkanes, mentane, menthone, menthol, terpinene, D-terpinene, dipentene, N-nonalol and limonene.

The skin penetration enhancing systems of the invention may further comprise one or more of a surfactant, stiffening agent, preservative, pH adjuster, antioxidant, or solvent.

Examples of surfactants include compounds useful as surface active agents, such as cleansing agents, emulsifying agents, foam boosters, solubilizing agents, suspending agents, and hydrotropes. Examples of surfactants include anionic and cationic surfactants such as ammonium and sulfate-derived surfactants. Examples of non-ionic surfactants include surfactants such as sorbitan, polysorbate, steareth, and polyethylene glycol-derived surfactants.

Examples of non-ionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbons in the alkyl chain condensed with 2 to 20 moles of ethylene oxide, mono- and di-acyl esters of ethylene glycol, wherein the fatty acid contains from 10 to 20 carbons, monoglycerides wherein the fatty acid contains from 10 to 20 carbons, diethylene glycol, polyethylene glycols of molecular weight 200 to 6000, polypropylene glycol of molecular weight 200 to 3000, glycerol, sorbitol, sorbitan, polyoxyethylene sorbitol, polyoxyethylene sorbitan and hydrophilic wax esters. Suitable anionic emulsifiers include, but are not limited to, fatty acids saponified (soaps) with potassium, sodium, or triethanolamine, wherein the fatty acid contains from 10 to 20 carbons. Other suitable anionic emulsifiers include, but are not limited to, alkali metals, ammonium or substituted ammonium with alkyl sulfates, alkyl arylsulfonates and alkyl ethoxy ether sulfonates having 10 to 30 carbons in the alkyl chain and from 1 to 50 ethylene oxide units. Suitable cationic emulsifiers include quaternary ammonium and morpholinium and pyridinium compounds.

A stiffening agent is an agent capable of stiffening a formulation of the invention, for example, by increasing the viscosity of the formulation. Examples of suitable stiffening agents include gelling agents, waxes, and long chain hydrocarbons (e.g., $C_9$-$C_{18}$ alcohols). For example, suitable stiffening agents include fatty alcohols such as stearyl alcohol and cetyl alcohol.

Examples of preservatives suitable for use in the formulations of the invention include any compound useful to prevent or retard microbial growth. Examples include cationic and nonionic preservatives, such as benzalkonium chloride, methyl and ethyl paraben, p-hydroxy-benzoates (parabens), and benzoic acid.

Examples of pH adjusters include acids, bases, or buffering agents that may be used to control the pH of finished products, such as citrate, ascorbate, and phosphate buffers. Buffering systems include, for example, systems selected from the group consisting of acetic acid/acetate, malic acid/malate, citric acid/citrate, tartaric acid/tartrate, lactic acid/lactate, phosphoric acid/phosphate, glycine/glycimate, tris, glutamic acid/glutamates, and sodium carbonate. Suitable ranges for pH include from about 3.0 to about 8.0.

Examples of antioxidants suitable for use in the formulations of the invention include any compound used to prevent or retard product spoilage from rancidity or from reaction with oxygen, such as reducing agents and free radical scavengers (e.g., sulfur-derived antioxidants and chelating agents).

The terms "excipient" or "vehicle" refer to vehicle materials suitable for compound administration and include any such material known in the art such as, for example, any liquid, gel, solvent, liquid diluent, solubilizer, or the like. Typically, an excipient employed in a formulation of the invention will have no irritancy or toxicity to the skin.

Additives usually found in topical compositions, such as dyes and perfumes, may be included in any of the formulations described herein.

In some embodiments, a formulation of the invention comprises potassium 2,5-dihydroxybenzenesulfonate, about 0.1 to about 99% of at least one occlusive agent, and about 0.1 to about 5% of at least one surfactant.

In certain embodiments, a formulation of the invention comprises about 0.1 to about 20.0% potassium 2,5-dihydroxybenzenesulfonate, about 0.1 to about 90.0% white petrolatum, about 0.1 to about 90.0% mineral oil, about 0.1 to about 50.0% stearyl alcohol, about 0.05 to about 50% cetyl alcohol, about 0.1 to about 5% steareth-2 (Brij 72), and about 0.1 to about 5% steareth-21 (Brij 721). In yet other embodiments, a formulation of the invention further comprises about 0.1 to about 5% benzyl alcohol, about 0.001 to about 0.5% sodium thiosulfate pentahydrate, about 0.01 to about 10% acetic acid, about 0.001% to 1.0% sodium acetate, and about 0 to 90.0% water.

In a particular embodiment, a formulation comprises about 0 to about 10% potassium 2,5-dihydroxybenzenesulfonate, about 20% white petrolatum, about 20% mineral oil, about 2.5% stearyl alcohol, about 0.5% cetyl alcohol, about 1.0% steareth-2, about 4.0% steareth-21, about 0.5% benzyl alcohol, about 0.1% sodium thiosulfate pentahydrate, about 0.05% acetic acid, about 0.02% sodium acetate, and a sufficient quantity of water to make a final concentration of 100%.

The skin penetration enhancing systems disclosed herein are capable of enhancing penetration of one or more polar or ionic drugs through one or more layers of skin, such as human skin. In some embodiments, a formulation of the invention is capable of enhancing penetration of a polar or ionic drug through the epidermis. In further embodiments, a formulation of the invention is capable of enhancing penetration of a polar or ionic drug through the dermis. In yet other embodiments, a formulation of the invention is capable of enhancing transdermal penetration of a polar or ionic drug.

Bioavailability following topical application in vivo can be assessed using in vitro percutaneous absorption test methods. Suitable methods include those described in the FDA and AAPS Report of the Workshop on Principles and Practices of In Vitro Percutaneous Penetration Studies: Relevance to Bioavailability and Bioequivalence (Skelly et al., Pharm. Res. 4(3):265-267 (1987)), incorporated herein by reference.

The skin penetration enhancing systems disclosed herein are suitable for enhancing the skin penetration of a number of polar drugs useful in the treatment of one or more disorders. For example, in embodiments wherein the active pharmaceutical agent is potassium 2,5-dihydroxybenzenesulfonate, disorders that may be treated by topical administration of a formulation of the invention include rosacea, acne, cancers of the skin (e.g., basal cell carcinoma), actinic keratosis, dermatitis (e.g., contact dermatitis and atopic dermatitis), and psoriasis. Examples of disorders that may be treated by a formulation of the invention comprising a 2,5-dihydroxybenzene derivative are disclosed in U.S. application Ser. Nos. 10/588,166; 11/506,469; 11/839,508; 11/839,512; 11/839,515; 11/839,520; 11/839,522; and International Application Serial Nos. PCT/EP2007/058447; PCT/EP2007/058444; PCT/EP2007/058445; PCT/EP2007/058446; PCT/EP2007/058451; PCT/EP2007/058453; PCT/EP2007/058454; and PCT/EP2007/058456, each of which is incorporated herein by reference.

The effective amount of an active pharmaceutical agent, such as potassium 2,5-dihydroxybenzenesulfonate, in a formulation of the invention used topically will vary according to the specific circumstances of application, the duration of exposure and similar considerations. For example, therapeutic amounts can be empirically determined and will vary with the particular condition being treated, the intactness of the skin, the type of skin or mucosal tissue that is being treated, the nature of the active pharmaceutical agent, the particular formulation components, dosage form, and the like. Generally, the amount will vary from 0.01 microgram to 50 milligrams of a polar compound, such as a compound of Formula (I), per square centimeter of the epidermis area. A typical range for application volume is about 3 to about 10 microliters per square centimeter. Factors that will influence the application amount include the spreadability of the formulation, which is usually directly proportional to the viscosity of the formulation. The amount of topical composition (e.g., a compound of Formula (I) and a vehicle) applied on the affected area may be easily determined according to the amount of compound contained therein.

Administration of a formulation of the invention may be intermittent in time and may be administered daily, weekly, biweekly, monthly, bimonthly, quarterly, or even for longer durations of time. The time period between treatments depends upon factors such as the disorder being treated, the degree of disease progression, and the type of skin being treated. It is well within the skill level of the practitioner to determine a specific administration period for a particular situation.

Topical administration includes depositing or spreading a formulation of the invention over stratified epithelia (including skin, corneal, otic, and mucosal tissues, such as oral, gingival, nasal, urethral, bladder, rectal, vulvar, vaginal, and uterine tissues).

The skin penetration enhancing systems described herein may be formulated in any form suitable for topical administration, such as lotions, creams, solutions, sprays, and the like. The formulation may comprise an aqueous phase and an oil phase. In some embodiments, the systems are formulated in an emulsion. The system may be an emulsion or may be used in the manufacture of an emulsion. It may, for example, be from or be comprised in the aqueous phase of an emulsion. If an emulsion, the composition will typically be an oil-in-water emulsion, but in certain embodiments, the emulsion may alternatively be a water-in-oil emulsion.

In some embodiments, the systems are formulated in a cream. In other embodiments, the systems are formulated in a solution. In yet other embodiments, the systems of the invention are formulated in a spray.

Lotions

Typically, lotions will contain from about 0.001% to about 30% of a polar compound, for example, a compound of Formula: (I), and will further contain from about 1% to about 25% of an emollient and the appropriate amount of water.

Examples of emollients include:

Hydrocarbon waxes and oils such as mineral oils, petrolatum, paraffin, ceresin, microcrystalline wax, polyethylene and perhydrosqualene.

Silicone oils such as dimethylpolysiloxanes, methylphenylpolysiloxanes and water-soluble and alcohol-soluble glycol-silicone copolymers.

Triglycerides, such as animal and vegetable fats and oils. Examples include, but are not limited to, castor oil, cod liver oil, corn oil, olive oil, almond oil, palm oil, sesame oil, cotton seed oil and soybean oil.

Acetoglyceride esters, such as acetylated monoglycerides.

Ethoxylated glycerides, such as ethoxylated glycerol monostearate.

Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristoyl lactate and cetyl lactate.

Alkenyl esters of fatty acids having 10 to 20 carbon atoms. Examples thereof include, but are not limited to, oleyl myristate, oleyl stearate and oleyl oleate.

Fatty acids having 10 to 20 carbon atoms. Suitable examples include, but are not limited to, pelargonic, lauric, myristic, palmitic, stearic, isostearic, hydroxystearic, oleic, linoleic, ricinoleic, arachidonic, behenic and erucic acids.

Fatty alcohols having 10 to 20 carbon atoms. Lauryl, myristoyl, palmitoyl, stearyl, isostearyl, hydroxystearyl, oleyl, ricinoleyl, behenyl, erucyl and 2-octyl dodecanol alcohols are appropriate examples of fatty alcohols.

Fatty alcohol ethers. Ethoxylated fatty alcohols having 10 to 20 carbon atoms include, but are not limited to, lauryl, cetyl, stearyl, isostearyl, oleyl and cholesterol alcohols having attached thereto from 1 to 50 ethylene oxide groups or 1 to 50 propylene oxide groups.

Ether-esters, such as fatty acid esters of ethoxylated fatty alcohols.

Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleates, lanolin alcohols ricinoleate, acetate of lanolin alcohols ricinoleate, hydrogenolysis of lanolin, and liquid or semisolid lanolin absorption bases are illustrative examples of lanolin derived emollients.

Polyhydric alcohols and polyether derivatives. Propylene glycol, dipropylene glycol, polypropylene glycol 2000 and 4000, polyoxyethylene polypropylene glycols, glycerol, ethoxylated glycerol, propoxylated glycerol, sorbitol, ethoxylated sorbitol, hydroxypropyl sorbitol, polyethylene glycol 200-6000, methoxy polyethylene glycols 350, 550, 750, 2000, 5000, poly(ethylene oxide) homopolymers (100,000-5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), and polyoxypropylene derivatives of trimethylolpropane are suitable examples.

Polyhydric alcohol esters. Mono- and di-acyl esters of ethylene glycol, mono- and di-acyl esters of diethylene glycol, mono- and di-acyl esters of polyethylene glycol (200-6000), mono- and di-acyl esters of propylene glycol, polypropylene glycol 2000 monooleate, polypropylene glycol 2000 monostearate, ethoxylated propylene glycol monostearate, mono- and di-acyl esters of glycerol, polyacyl esters of poly glycerol, ethoxylated glycerol monostearate, 1,3-butylene glycol monostearate, 1,3-butylene glycol distearate, acyl ester of polyoxyethylene polyol, acyl esters of sorbitan, and acyl esters of polyoxyethylene sorbitan are suitable examples.

Waxes such as beeswax, spermaceti, myristoyl myristate and stearyl stearate.

Beeswax derivatives, such as polyoxyethylene sorbitol beeswax. These are reaction products of beeswax with ethoxylated sorbitol of varying ethylene oxide content that form a mixture of ether-esters.

Vegetable waxes, including, but not limited to, carnauba and candelilla waxes.

Phospholipids such as lecithin and derivatives.

Sterols. Examples include, but are not limited to, cholesterol and acyl esters of cholesterol.

Amides, such as fatty acid amides, ethoxylated acyl amides and solid fatty acid alkanolamides.

In some embodiment, the lotions of the invention further contain from about 1% to about 30% of an emulsifier. The emulsifiers can be anionic, cationic or non-ionic.

Some emollients previously described also have emulsifying properties. When a lotion contains one of these emollients, an additional emulsifier may not be needed, though it can be included in the formulation.

The balance of the composition is generally water. The lotions are formulated by simply admixing all of the components together. In some embodiments, the polar compound, for example, a compound of Formula (I), is dissolved in the emollient and the resulting mixture is added into the water. Optional components such as the emulsifier or other additives may be included in the composition. One such additive is a thickening agent included at a level of 1% to 30% by weight of the composition. Examples of suitable thickening agents are: cross-linked carboxypolymethylene polymers, methyl cellulose, polyethylene glycols, gums and bentonite.

Creams

The compositions of the present invention may be also formulated in the form of a cream. Creams will typically contain from about 0.001% to about 30% of a polar compound, for example, a compound of Formula (I). Creams will typically further contain from about 5% to about 50% of an emollient and the remainder is water. The emollients, as described above, can also be used in the cream formulation. Optionally, the cream may contain an emulsifier at a level from about 3% to about 50%. The previously described emulsifiers would also be adequate in this case.

Solutions

The compositions of the present invention may also be formulated in the form of a solution. Solutions typically contain from about 0.001% to about 30% of a polar compound, such as a compound of Formula (I), and an adequate amount of an organic solvent. Organic substances useful as a solvent or a part of a solvent system are as follows: propylene glycol, polyethylene glycol (200-600), polypropylene glycol (425-2025), glycerine, sorbitol esters, 1,2,6-hexanetriol, ethanol, isopropanol, diethyl tartrate, butanediol, and mixtures thereof. Such solvent systems can also contain water. These compositions are applied on the skin in the form of a solution, or solutions are formulated in the form of aerosol and applied on the skin as a spray. Compositions in the form of aerosol additionally contain from 25% to 80% of a suitable propellant. Examples of propellants include, but are not limited to: chlorinated, fluorinated and fluorochlorinated low molecular weight hydrocarbons. Nitrous oxide and carbon dioxide are also used as propellant gases. Enough quantity to expel the content of the cartridge is used.

Gels

The composition in the form of a gel might be simply obtained by the addition of a suitable thickening agent to the composition in the form of a solution as described above. Suitable thickening agents have been described above regarding lotions.

Gel formulations typically contain from about 0.001% to about 30% of a polar compound, such as a compound of Formula (I), 5% to 75% of a suitable organic solvent, 0.5% to 20% of a suitable thickening agent, and an appropriate amount of water and the like.

Solids

The compositions in the present invention may also be formulated in solid form. Such forms may have the shape of a bar intended for the application on the lips or other parts of the body. These compositions will generally contain from about 0.001% to about 30% of a polar compound, such as a compound of Formula (I), and from about 50% to about 98% of an emollient such as those discussed above. The composition may further contain from about 1% to about 20% of a suitable thickening agent, such as those already described, and, optionally, an emulsifier and water.

A formulation of the invention may be prepared by methods well known to those skilled in the art. For example, a formulation of the invention that is an emulsion may be prepared by heating the oils to about 70° C., then adding them steadily to the water phase, which is also at or about 70° C., with stirring, and then allowing the emulsion to cool.

In certain embodiments, once an emulsion has been formed, further water may be added with stirring if desired, for example in preparing a formulation suitable for delivery as a foam. A suitable formulation for delivery as a foam may be prepared by diluting an emulsion essentially as described above by the addition of one part water to two parts emulsion. It will be appreciated that if an emulsion is to be diluted before application to the skin that it may be preferred that the concentration of the drug, for example potassium 2,5-dihydroxybenzenesulfonate, in the emulsion may be calculated such that the desired concentration, for example 10%, is achieved in the diluted formulation. In certain further embodiments, the emulsion is formed with the composition that it is intended to apply to the skin, for example with the additional water referred to above ab initio so that dilution is not necessary.

In another embodiment, a formulation of the invention is a solution that may be prepared by dissolving the active pharmaceutical agent in a solvent, such as water, and adding any remaining ingredients to the solution by stirring and heating, for example, to temperatures of about 70° C. After a homogeneous mixture is achieved, the solution may then be allowed to cool, for example by placement in a cool water bath, and mixed until temperatures are below about, for example, 40° C.

In yet other embodiments, a formulation of the invention is a suspension that may be prepared by dissolving any excipients in a solvent, such as water, with stirring and heating as necessary, for example, to temperatures of about 70° C., and then adding the active pharmaceutical agent to the homogeneous mixture and mixing until homogeneity appears to be achieved. The mixture may then be cooled until temperatures are below about, for example, 40° C.

The following non-limiting examples further describe and enable one of ordinary skill in the art to make and use the present invention.

EXAMPLES

Example 1. In Vitro Percutaneous Absorption of 2,5-dihydroxybenzenesulfonate from Various Formulations Methods An in vitro percutaneous absorption study evaluated tissue permeation and penetration of 2,5-dihydroxybenzenesulfonate from various formulations along with controls 10% Calcium Dobesilate in DMSO and Doxiproct® Ointment (4% Calcium Dobesilate). The composition of the formulations evaluated in this study is summarized below.

Formulations

A. ID: 2567-20A (Calcium Dobesilate, 10% in DMSO). DMSO is known to provide the maximum skin permeability of many pharmaceutical ingredients.
B. ID: Doxiproct® Ointment (4% Calcium Dobesilate, Lot # OM Portuguesa, S.A. 151065) PEG (polyethylene glycol) Base ointment. Commercially available for the treatment of hemorrhoids.
C. ID: 2567-19B (Cream, 5% Potassium 2,5-dihydroxybenzenesulfonate). The active pharmaceutical ingredient (API) is introduced to the base formulation via spatulation.
Formulations D-F: Propylene glycol, transcutol and a combination thereof as primary delivery systems.
Formulations G and H: An alternate delivery system. The combination of propylene glycol and ethanol is commonly used in delivering molecules through the stratum corneum.
Formulations I and J: The concentrations listed of both the calcium and potassium salts of 2,5-dihydroxybenzenesulfonate are based on the molar concentration of 2,5-dihydroxybenzenesulfonate present. (Molecular weight (MW) of Calcium Dobesilate Monohydrate is 436.4 and MW of Potassium 2,5-dihydroxybenzenesulfonate is 228.3).

TABLE 1

Formulation Compositions

| Ingredients | % w/w | | | | | | | |
|---|---|---|---|---|---|---|---|---|
| | C | D | E | F | G | H | I | J |
| Formulation ID #: 2567- | 19B | 16A | 16B | 17A | 17B | 18A | 19A | 18B |
| Calcium Dobesilate Monohydrate | — | 10.0 | 10.0 | 10.0 | 10.0 | 10.0 | — | 4.8 |
| Potassium 2,5-dihydroxybenzenesulfonate | 5.0 | — | — | — | — | — | 5.0 | — |
| Cetyl Alcohol | 2.5 | — | — | — | — | — | — | — |
| Stearyl Alcohol | 2.5 | — | — | — | — | — | — | — |
| Mineral Oil | 30.0 | — | — | — | — | — | — | — |
| White Petrolatum | 20.0 | — | — | — | — | — | — | — |
| Propylene Glycol | — | 20.0 | 20.0 | — | 20.0 | 10.0 | 20.0 | 20.0 |
| Span 80 | 5.0 | — | — | — | — | — | — | — |
| Transcutol | — | — | 10.0 | 20.0 | — | — | 10.0 | 10.0 |
| Ethanol 190 Proof | — | — | — | — | 10.0 | 10.0 | — | — |
| Sodium Thiosulfate, Pentahydrate | — | 0.05 | 0.05 | 0.05 | 0.05 | 0.05 | 0.05 | 0.05 |
| Benzyl Alcohol | — | — | — | 1.0 | — | 1.0 | — | — |
| Disodium Edetate, Dihydrate | — | 0.5 | 0.5 | 0.5 | 0.5 | 0.5 | 0.5 | 0.5 |
| 100 mM Acetate Buffer (pH 4.0) | — | 10.0 | 10.0 | 10.0 | 10.0 | 10.0 | 10.0 | 10.0 |
| Hydroxyethyl Cellulose, 250HHX | — | 1.2 | 1.2 | 1.2 | 1.2 | 1.2 | 1.2 | 1.2 |
| Purified Water | 35.0 | 58.25 | 48.25 | 57.25 | 48.25 | 57.25 | 53.25 | 53.45 |

The clinically relevant dose of 5 mg/cm² was applied to dermatomed human abdominal tissue from a single donor obtained following elective surgery. The thickness of the tissue ranged from 0.023-0.038 inches (0.584-0.965 mm) with a mean +/− standard deviation in thickness of 0.029+/−0.005 inches (0.740+/−0.130 mm) and a coefficient of variation of 17.6%.

Percutaneous absorption was evaluated using this human abdominal skin mounted in Bronaugh flow-through diffusion cells. The cells were maintained at a constant temperature of 32° C. by use of recirculating water baths. These cells have a nominal diffusion area of 0.64 cm². Fresh receptor phase, PBS with 0.1% sodium azide and 4% Bovine Serum Albumin, was continuously pumped under the tissue at a flow rate of nominally 1.5 ml/hr and collected in 6-hour intervals. The receptor phase samples were collected and transferred into tared scintillation vials. Following the 24-hour duration exposure, the formulation residing on the tissue surface was removed by tape-stripping with CuDerm D-Squame stripping discs.

The epidermis, dermis, and receptor phase samples were subsequently analyzed for 2,5-dihydroxybenzenesulfonate (dobesilate) content. All analytical results for dobesilate content in the study samples were reported in units of calcium dobesilate-equivalents where 10 mg of calcium dobesilate contains 8.67 mg of free dobesilate and 10 mg of potassium 2,5-dihydroxybenzenesulfonate contains 8.29 mg of free dobesilate.

The mass of 2,5-dihydroxybenzenesulfonate per square centimeter of tissue was calculated using the mass of 2,5-dihydroxybenzenesulfonate in the sample divided by the area of application.

Tissue permeation and deposition results were statistically evaluated using unpaired student's t-tests (significant differences between formulations were defined by a p-value of <0.05, at the 95% confidence interval).

Results

Tissue permeation (receptor phase levels) of 2,5-dihydroxybenzenesulfonate ranged from 0.00 to 8.57 percent of the applied dose over the 24 hour duration of exposure. The highest level of 2,5-dihydroxybenzenesulfonate permeation was observed with the DMSO solution (Formulation 2567-20A) followed by Formulation 2567-19B. Very little or no 2,5-dihydroxybenzenesulfonate was observed permeating the skin from the remaining formulations, including the commercial product, Doxiproct® Ointment. The kinetic profile of tissue permeation is presented in FIGS. 1 and 2 where the cumulative tissue permeation of 2,5-dihydroxybenzenesulfonate units of ng/cm² is plotted against time in time (hours).

Tissue levels of 2,5-dihydroxybenzenesulfonate were measured at the end of the exposure period. Epidermal deposition of 2,5-dihydroxybenzenesulfonate following the 24-hour duration of exposure ranged from 2.64 to 30.1 percent of the applied dose. The DMSO solution, Doxiproct® Ointment and Formulation 2567-19B had the highest residual percentage of applied 2,5-dihydroxybenzenesulfonate in the epidermis. Dermal deposition of 2,5-dihydroxybenzenesulfonate ranged from below detection to 1.24 percent of the applied dose. The DMSO solution and Formulation 2567-19B had the highest residual percentage of applied 2,5-dihydroxybenzenesulfonate retained in the dermis. Epidermal levels of 2,5-dihydroxybenzenesulfonate following topical exposure are graphically summarized in FIG. 3 in units of μg/cm². Dermal levels of 2,5-dihydroxybenzenesulfonate following topical exposure are graphically summarized in FIG. 4 in units of μg/cm².

Tissue permeation and deposition of 2,5-dihydroxybenzenesulfonate are summarized in Table 2, in units of mass and mass/cm², and percent of applied dose. Tissue deposition and penetration of 2,5-dihydroxybenzenesulfonate were statistically evaluated using unpaired student's t-tests (significant differences between formulations were defined by a p-value of <0.05, at the 95% confidence interval). Results of the statistical analysis are summarized in Tables 3A and 3B.

The DMSO solution and Formulation 2567-19B had the highest skin permeation and tissue deposition of applied 2,5-dihydroxybenzenesulfonate relative to the other formulations tested. The non-DMSO containing formulations did not afford comparable skin delivery levels of 2,5-dihydroxybenzenesulfonate relative to that from Formulation 2567-19B.

Reference

Skelly, J. P., Shah, V. P., Maibach, H. I., Guy, R. H., Wester, R. C., Flynn, G. L. and Yacobi, A. (1987). "FDA and AAPS report of the workshop on principles and practices of in-vitro percutaneous penetration studies: Relevance to bioavailability and bioequivalence." Pharmaceutical Research 4(3): 265-267.

TABLE 2

Cumulative Receptor Phase and Tissue Levels of Dobesilate Following 24 Hours of Topical Exposure

| Formulation ID | | Receptor Content at 24 Hours | | Epidermis | | Dermis | |
|---|---|---|---|---|---|---|---|
| | | (ng/cm²) | (% Dose Applied) | (μg/cm²) | (% Dose Applied) | (μg/cm²) | (% Dose Applied) |
| A) ID: 2567-20A | Mean | 47299 | 8.57 | 164.4 | 30.11 | 6.83 | 1.24 |
| | SD | 14828 | 2.45 | 66.7 | 12.82 | 10.02 | 1.79 |
| | % CV | 31 | 29 | 41 | 43 | 147 | 145 |
| B) ID: Doxiproct Ointment | Mean | 0.0000 | 0.0000 | 64.1 | 29.86 | 0.432 | 0.198 |
| | SD | 0.0000 | 0.0000 | 21.2 | 9.86 | 0.433 | 0.197 |
| | % CV | N/A | N/A | 33 | 33 | 100 | 99 |
| C) ID: 2567-19B | Mean | 4894 | 1.93 | 60.0 | 26.06 | 1.009 | 0.452 |
| | SD | 4322 | 1.59 | 15.0 | 7.27 | 0.368 | 0.202 |
| | % CV | 88 | 82 | 25 | 28 | 36 | 45 |
| D) ID: 2567-16A | Mean | 1203 | 0.231 | 28.9 | 5.59 | 0.170 | 0.0333 |
| | SD | 1358 | 0.263 | 29.4 | 5.78 | 0.381 | 0.0745 |
| | % CV | 113 | 114 | 102 | 103 | 224 | 224 |
| E) ID: 2567-16B | Mean | 0.0000 | 0.0000 | 56.5 | 11.34 | 1.06 | 0.211 |
| | SD | 0.0000 | 0.0000 | 26.6 | 5.27 | 1.55 | 0.308 |
| | % CV | N/A | N/A | 47 | 47 | 146 | 146 |

TABLE 2-continued

Cumulative Receptor Phase and Tissue Levels of Dobesilate Following 24 Hours of Topical Exposure

| Formulation | | Receptor Content at 24 Hours | | Epidermis | | Dermis | |
|---|---|---|---|---|---|---|---|
| ID | | (ng/cm$^2$) | (% Dose Applied) | (μg/cm$^2$) | (% Dose Applied) | (μg/cm$^2$) | (% Dose Applied) |
| F) ID: 2567-17A | Mean | 0.0000 | 0.0000 | 38.7 | 7.81 | 3.11 | 0.596 |
| | SD | 0.0000 | 0.0000 | 19.2 | 3.79 | 6.10 | 1.156 |
| | % CV | N/A | N/A | 50 | 49 | 196 | 194 |
| G) ID: 2567-17B | Mean | 362 | 0.0730 | 18.40 | 3.80 | 0.0000 | 0.0000 |
| | SD | 369 | 0.0740 | 8.86 | 1.94 | 0.0000 | 0.0000 |
| | % CV | 102 | 101 | 48 | 51 | N/A | N/A |
| H) ID: 2567-18A | Mean | 211 | 0.0412 | 25.6 | 4.96 | 0.600 | 0.115 |
| | SD | 293 | 0.0575 | 17.0 | 3.27 | 1.342 | 0.256 |
| | % CV | 139 | 139 | 66 | 66 | 224 | 224 |
| I) ID: 2567-19A | Mean | 0.0000 | 0.0000 | 13.98 | 5.50 | 0.0000 | 0.0000 |
| | SD | 0.0000 | 0.0000 | 5.85 | 2.32 | 0.0000 | 0.0000 |
| | % CV | N/A | N/A | 42 | 42 | N/A | N/A |
| J) ID: 2567-18B | Mean | 0.0000 | 0.0000 | 6.39 | 2.64 | 0.0000 | 0.0000 |
| | SD | 0.0000 | 0.0000 | 3.92 | 1.72 | 0.0000 | 0.0000 |
| | % CV | N/A | N/A | 61 | 65 | N/A | N/A |

Tables 3A and B. Cumulative Receptor Phase Statistical Analysis of Dobesilate in ng/cm$^2$ (Table 3A) and Percent of Applied Dose (Table 3B)

TABLE 3A

Unpaired T-Test of Receptor Phase Presented in p values

| From: To | ID: 2567-20A | ID: Doxiproct Ointment | ID: 2567-19B | ID: 2567-16A | ID: 2567-16B | ID: 2567-17A | ID: 2567-17B | ID: 2567-18A | ID: 2567-19A |
|---|---|---|---|---|---|---|---|---|---|
| ID: Doxiproct Ointment | 0.0001 | — | — | — | — | — | — | — | — |
| ID: 2567-19B | 0.0003 | 0.0352 | — | — | — | — | — | — | — |
| ID: 2567-16A | 0.0001 | 0.0828 | 0.106 | — | — | — | — | — | — |
| ID: 2567-16B | 0.0001 | N/A | 0.0352 | 0.0828 | — | — | — | — | — |
| ID: 2567-17A | 0.0001 | N/A | 0.0352 | 0.0828 | N/A | — | — | — | — |
| ID: 2567-17B | 0.0001 | 0.0593 | 0.0477 | 0.218 | 0.0593 | 0.0593 | — | — | — |
| ID: 2567-18A | 0.0001 | 0.146 | 0.0421 | 0.149 | 0.146 | 0.146 | 0.494 | — | — |
| ID: 2567-19A | 0.0001 | N/A | 0.0352 | 0.0828 | N/A | N/A | 0.0593 | 0.146 | — |
| ID: 2567-18B | 0.0001 | N/A | 0.0352 | 0.0828 | N/A | N/A | 0.0593 | 0.146 | N/A |

TABLE 3B

Unpaired T-Test of Receptor Phase Presented in p values

| From: To | ID: 2567-20A | ID: Doxiproct Ointment | ID: 2567-19B | ID: 2567-16A | ID: 2567-16B | ID: 2567-17A | ID: 2567-17B | ID: 2567-18A | ID: 2567-19A |
|---|---|---|---|---|---|---|---|---|---|
| ID: Doxiproct Ointment | 0.0001 | — | — | — | — | — | — | — | — |
| ID: 2567-19B | 0.0009 | 0.0261 | — | — | — | — | — | — | — |
| ID: 2567-16A | 0.0001 | 0.0852 | 0.0456 | — | — | — | — | — | — |
| ID: 2567-16B | 0.0001 | N/A | 0.0261 | 0.0852 | — | — | — | — | — |
| ID: 2567-17A | 0.0001 | N/A | 0.0261 | 0.0852 | N/A | — | — | — | — |

TABLE 3B-continued

Unpaired T-Test of Receptor Phase
Presented in p values

| From: To | ID: 2567-20A | ID: Doxiproct Ointment | ID: 2567-19B | ID: 2567-16A | ID: 2567-16B | ID: 2567-17A | ID: 2567-17B | ID: 2567-18A | ID: 2567-19A |
|---|---|---|---|---|---|---|---|---|---|
| ID: 2567-17B | 0.0001 | 0.0585 | 0.0308 | 0.232 | 0.0585 | 0.0585 | — | — | — |
| ID: 2567-18A | 0.0001 | 0.147 | 0.0286 | 0.154 | 0.147 | 0.147 | 0.470 | — | — |
| ID: 2567-19A | 0.0001 | N/A | 0.0261 | 0.0852 | N/A | N/A | 0.0585 | 0.147 | — |
| ID: 2567-18B | 0.0001 | N/A | 0.0261 | 0.0852 | N/A | N/A | 0.0585 | 0.147 | N/A |

Example 2. In Vitro Percutaneous Absorption of Potassium 2,5-dihydroxybenzenesulfonate from Various Formulations Formulations were tested that differ in the approach used for physically stabilizing Formulation 2567-95 (shown in Table 4 below). The in vitro percutaneous absorption of 2,5-dihydroxybenzenesulfonate was characterized from eight formulations at 10% potassium 2,5-dihydroxybenzenesulfonate and one reference formulation (Formulation 2567-95, 5% potassium 2,5-dihydroxybenzenesulfonate) following topical application to excised human skin from elective surgery.

Methods

This in vitro percutaneous absorption study evaluated tissue permeation and penetration of 2,5-dihydroxybenzenesulfonate from various formulations. The composition of each of the formulations evaluated in this study is summarized in Table 4.

The clinically relevant dose of 5 mg/cm² was applied to dermatomed human abdominal tissue from a single donor obtained following elective surgery. The thickness of the tissue ranged from 0.022-0.035 inches (0.559-0.889 mm) with a mean +/− standard deviation in thickness of 0.030+/−0.004 inches (0.760+/−0.095 mm) and a coefficient of variation of 12.5%.

Percutaneous absorption was evaluated using this human abdominal tissue from a single donor mounted in Bronaugh flow-through diffusion cells. The cells were maintained at a constant temperature of 32° C. by use of recirculating water baths. These cells have a nominal diffusion area of 0.64 cm². Fresh receptor phase, PBS with 0.1% sodium azide and 4% Bovine Serum Albumin, was continuously pumped under the tissue at a flow rate of nominally 1.0 ml/hr and collected in 6-hour intervals. The receptor phase samples were collected and transferred into tared scintillation vials. Following the 24-hour duration exposure, the formulation residing on the tissue surface was removed by tape-stripping with CuDerm D-Squame stripping discs. The amount of 2,5-dihydroxybenzenesulfonate residing in the tape-strips, epidermis, dermis, and receptor phase samples were subsequently analyzed for 2,5-dihydroxybenzenesulfonate content.

TABLE 4

Formulation Compositions

| | 1 | 2 | 3 | 4 | 5 | 6 | 7 | 8 | 9 |
|---|---|---|---|---|---|---|---|---|---|
| | | | | Lot # 2567- | | | | | |
| Ingredients | 95 Control | 86 | 89 | 87 In Solution | 91 | 90 | 92 | 93 Suspended | 94 |
| Potassium Dobesilate | 5 | 10 | 10 | 10 | 10 | 10 | 10 | 10 | 10 |
| Cetyl Alcohol | 2.5 | 0.5 | 0.5 | 0.5 | 0.5 | 0.5 | 0.5 | 0.5 | 0.5 |
| Stearyl Alcohol | 2.5 | 2.5 | 2.5 | 2.5 | 2.5 | 2.5 | 2.5 | 2.5 | 2.5 |
| Mineral Oil | 30 | 20 | 20 | 20 | 20 | 20 | 20 | 20 | 20 |
| White Petrolatum | 20 | 20 | 20 | 20 | 20 | 20 | 20 | 20 | 20 |
| Propylene Glycol | — | — | — | — | — | — | — | — | 10 |
| Span 80 | 5 | — | — | — | — | — | — | — | — |
| Span 60 | — | 2.5 | 2.5 | — | — | — | — | — | — |
| Tween 60 | — | 2.5 | 2.5 | — | — | — | — | — | — |
| Brij 72 | — | — | — | 1 | 1 | 1 | 1 | 1 | 1 |
| Brij 721 | — | — | — | 4 | 4 | 4 | 4 | 4 | 4 |
| Benzyl Alcohol | — | 0.5 | 0.5 | 0.5 | 0.5 | 0.5 | 0.5 | 0.5 | — |
| Acetylcysteine | — | — | — | — | 0.1 | — | — | — | — |
| Sodium Thiosulfate•5H₂O | — | 0.1 | 0.1 | 0.1 | — | 0.1 | 0.1 | 0.1 | 0.1 |
| HEC 250 HHX | — | — | — | — | — | 0.5 | — | — | — |
| 100 mM Acetate Buffer | — | 10 | — | 10 | 10 | — | 10 | 10 | 10 |
| Purified Water | 35 | 31.4 | 41.4 | 31.4 | 31.4 | 41.4 | 30.9 | 31.4 | 21.9 |

The mass of 2,5-dihydroxybenzenesulfonate per square centimeter of dosed tissue was calculated using the concentration of 2,5-dihydroxybenzenesulfonate in each sample and the mass of each receptor sample divided by the area.

Tissue permeation results were statistically evaluated using unpaired student's t-tests (significant differences between formulations were defined by a p-value of <0.05, at the 95% confidence interval).

Results

Tissue permeation (receptor phase levels) of 2,5-dihydroxybenzenesulfonate ranged from 8.13 µg/cm² to 25.0 µg/cm² of 2,5-dihydroxybenzenesulfonate from Formulations 2567-93 and 2567-87, respectively. Tissue permeation from the reference formulation, Formulation 2567-95, was 21.6 µg/cm² of 2,5-dihydroxybenzenesulfonate. Formulations 2567-86, 2567-89, 2567-87, 2567-90 and 2567-94 had comparable levels of 2,5-dihydroxybenzenesulfonate permeating the skin relative to the reference formulation. Delivery from these five formulations ranged from 19.3 to 25.0 µg/cm² of 2,5-dihydroxybenzenesulfonate. The remaining three Formulations 2567-91, 2567-92 and 2567-93 demonstrated permeation levels lower than the reference formulation. Their permeation ranged from 8.13 to 13.7 µg/cm². The kinetic profile of tissue permeation is presented in FIG. 5 where the cumulative tissue permeation of 2,5-dihydroxybenzenesulfonate in units of µg/cm² is plotted against time. Tissue permeation of 2,5-dihydroxybenzenesulfonate is summarized in Table 5.

The tissue penetration of 2,5-dihydroxybenzenesulfonate was statistically evaluated using unpaired student's t-tests. Results of the statistical analysis are summarized in Table 6.

Five of the tested formulations (Formulations 2567-86, 2567-89, 2567-87, 2567-90 and 2567-94) delivered comparable mass of 2,5-dihydroxybenzenesulfonate through dermatomed human skin relative to the reference formulation, Formulation 2567-95.

Reference

Skelly, J. P., Shah, V. P., Maibach, H. I., Guy, R. H., Wester, R. C., Flynn, G. L. and Yacobi, A. (1987). "FDA and AAPS report of the workshop on principles and practices of in-vitro percutaneous penetration studies: Relevance to bioavailability and bioequivalence." Pharmaceutical Research 4(3): 265-267.

TABLE 5

Cumulative Receptor Phase Levels of 2,5-dihydroxybenzenesulfonate Following 24 Hours of Topical Exposure

| Formulation ID | | Receptor Content at 24 Hours | |
|---|---|---|---|
| | | (µg/cm²) | (% Dose Applied) |
| A) ID: 2567-95 | Mean | 21.6 | 8.93 |
| | SD | 21.1 | 8.56 |
| | % CV | 98 | 96 |
| B) ID: 2567-86 | Mean | 20.9 | 4.40 |
| | SD | 17.0 | 3.56 |
| | % CV | 81 | 81 |
| C) ID: 2567-89 | Mean | 23.6 | 4.97 |
| | SD | 23.6 | 4.76 |
| | % CV | 100 | 96 |
| D) ID: 2567-87 | Mean | 25.0 | 5.16 |
| | SD | 20.9 | 4.26 |
| | % CV | 84 | 83 |
| E) ID: 2567-91 | Mean | 13.7 | 2.82 |
| | SD | 8.5 | 1.76 |
| | % CV | 62 | 62 |
| F) ID: 2567-90 | Mean | 19.3 | 3.89 |
| | SD | 15.6 | 3.23 |
| | % CV | 81 | 83 |
| G) ID: 2567-92 | Mean | 9.04 | 2.02 |
| | SD | 9.17 | 1.95 |
| | % CV | 101 | 97 |
| H) ID: 2567-93 | Mean | 8.13 | 1.79 |
| | SD | 4.19 | 0.92 |
| | % CV | 52 | 52 |
| I) ID: 2567-94 | Mean | 23.9 | 5.36 |
| | SD | 27.0 | 6.22 |
| | % CV | 113 | 116 |

Tables 6A and 6B. Cumulative Receptor Phase Statistical Analysis of 2,5-dihydroxybenzenesulfonate in µg/cm² (Table 6A) and Percent of Applied Dose (Table 6B)

TABLE 6A

Unpaired T-Test of Receptor Phase Presented in p values

| From: To | ID: 2567-95 | ID: 2567-86 | ID: 2567-89 | ID: 2567-87 | ID: 2567-91 | ID: 2567-90 | ID: 2567-92 | ID: 2567-93 |
|---|---|---|---|---|---|---|---|---|
| ID: 2567-95 | — | — | — | — | — | — | — | — |
| ID: 2567-86 | 0.951 | — | — | — | — | — | — | — |
| ID: 2567-89 | 0.876 | 0.820 | — | — | — | — | — | — |
| ID: 2567-87 | 0.782 | 0.713 | 0.916 | — | — | — | — | — |
| ID: 2567-91 | 0.418 | 0.378 | 0.355 | 0.248 | — | — | — | — |
| ID: 2567-90 | 0.834 | 0.868 | 0.712 | 0.600 | 0.461 | — | — | — |
| ID: 2567-92 | 0.212 | 0.165 | 0.188 | 0.117 | 0.380 | 0.196 | — | — |
| ID: 2567-93 | 0.157 | 0.105 | 0.144 | 0.081 | 0.177 | 0.121 | 0.829 | — |
| ID: 2567-94 | 0.874 | 0.823 | 0.988 | 0.935 | 0.401 | 0.726 | 0.232 | 0.189 |

TABLE 6B

Unpaired T-Test of Receptor Phase
Presented in p values

| From: To | ID: 2567-95 | ID: 2567-86 | ID: 2567-89 | ID: 2567-87 | ID: 2567-91 | ID: 2567-90 | ID: 2567-92 | ID: 2567-93 |
| --- | --- | --- | --- | --- | --- | --- | --- | --- |
| ID: 2567-95 | — | — | — | — | — | — | — | — |
| ID: 2567-86 | 0.258 | — | — | — | — | — | — | — |
| ID: 2567-89 | 0.346 | 0.817 | — | — | — | — | — | — |
| ID: 2567-87 | 0.358 | 0.742 | 0.943 | — | — | — | — | — |
| ID: 2567-91 | 0.118 | 0.354 | 0.324 | 0.242 | — | — | — | — |
| ID: 2567-90 | 0.207 | 0.801 | 0.654 | 0.572 | 0.493 | — | — | — |
| ID: 2567-92 | 0.083 | 0.182 | 0.190 | 0.131 | 0.471 | 0.253 | — | — |
| ID: 2567-93 | 0.070 | 0.113 | 0.139 | 0.087 | 0.231 | 0.156 | 0.800 | — |
| ID: 2567-94 | 0.428 | 0.749 | 0.907 | 0.951 | 0.359 | 0.619 | 0.239 | 0.195 |

Example 3. Formulation Preparation Methods

A formulation of the invention may be prepared using the non-limiting methods disclosed below, which are intended to illustrate certain embodiments of the invention.

Preparation of Formulation #2567-87, a solution, discussed above may be carried out as follows.

Formulation # 2567-87

| Ingredients | % w/w |
| --- | --- |
| A. DI Water | 31.4 |
| 100 mM Acetate Buffer (pH 4.0) | 10.0 |
| Sodium Thiosulfate, Penatahydrate | 0.1 |
| B. Potassium 2,5-dihydroxybenzenesulfonate | 10.0 |
| C. Benzyl Alcohol | 0.5 |
| D. Cetyl Alcohol | 0.5 |
| Stearyl Alcohol | 2.5 |
| White Petrolatum | 20.0 |
| Mineral Oil | 20.0 |
| Brij 72 | 1.0 |
| Brij 721 | 4.0 |

Procedure:

1. Combine ingredients in phase A in an appropriate size beaker and propeller mix until a solution is achieved (approximately 30 minutes).
2. In a laminar flow hood, add API in phase B to step 1. Once API is properly wetted, remove from hood and propeller mix until solution is achieved (approximately a few hours). Add heat (water bath) if necessary to speed up disillusion process. Heat to temperature no more that 70±5° C.
3. Add phase C to step 2 and propeller mix until solution is achieved (approximately 3 minutes).
4. In an appropriate size beaker combine ingredients in phase D.
5. Heat steps 3 and 4 to temperatures of no more than 70±5° C. (approximately 20 minutes)
6. Using silverson mixer, add step 3 to step 4 and mix until homogeneous mixture is achieved (5-10 minutes).
7. Transfer step 6 into a cool water bath and propeller mix until temperatures are below 40° C.

Preparation of Formulation #2567-93, a suspension, discussed above may be carried out as follows.

Formulation # 2567-93

| Ingredients | % w/w |
| --- | --- |
| A. DI Water | 31.4 |
| 100 mM Acetate Buffer (pH 4.0) | 10.0 |
| Sodium Thiosulfate, Penatahydrate | 0.1 |
| B. Benzyl Alcohol | 0.5 |
| C. Cetyl Alcohol | 0.5 |
| Stearyl Alcohol | 2.5 |
| White Petrolatum | 20.0 |
| Mineral Oil | 20.0 |
| Brij 72 | 1.0 |
| Brij 721 | 4.0 |
| D. Potassium 2,5-dihydroxybenzenesulfonate | 10.0 |

Procedure:

1. Combine ingredients in phase A in an appropriate size beaker and propeller mix until a solution is achieved (approximately 30 minutes).
2. Add phase B to step 1 and propeller mix until solution is achieved (approximately 3 minutes).
3. In an appropriate size beaker combine ingredients in phase C.
4. Heat steps 2 and 3 to temperatures of no more than 70±5° C. (approximately 20 minutes).
5. Using silverson mixer, add step 3 to step 4 and mix until homogeneous mixture is achieved (5-10 minutes).
6. With continuous mixing add API in step D to step 5. Mix until it appears to be homogeneous (5-10 minutes).
7. Transfer step 6 into a cool water bath and propeller mix until temperatures are below 40° C.

While specific embodiments of the subject invention have been discussed, the above specification is illustrative and not restrictive. One skilled in the art will appreciate that numerous changes and modifications can be made to the invention, and that such changes and modifications can be made without departing from the spirit and scope of the invention. The full scope of the invention should be determined by reference to the claims, along with their full scope of equivalents, and the specification, along with such variations.

Each patent, patent application, and publication cited or described in the present application is hereby incorporated by reference in its entirety as if each individual patent, patent application, or publication was specifically and individually indicated to be incorporated by reference.

What is claimed is:

1. A topical pharmaceutical skin penetration enhancing system, comprising a water-in-oil emulsion that comprises:
    (a) about 5 to about 10% by weight of potassium 2,5-dihydroxybenzenesulfonate (potassium dobesilate);
    (b) about 50 to about 75% by weight of at least one occlusive agent selected from white petrolatum, mineral oil, and mixtures thereof;
    (c) about 0.1 to about 5% by weight of at least one surfactant selected from steareth-2 (Brij 72), steareth-21 (Brij 721), and mixtures thereof;
    (d) about 0.1 to about 10% by weight of a stiffening agent selected from stearyl alcohol, cetyl alcohol, and mixtures thereof;
    (e) about 0.01 to about 10% by weight of a pH adjuster selected from acetic acid solution, sodium acetate, and mixtures thereof; and
    about 0.1 to less than about 22% by weight water.

2. The system of claim 1, further comprising a preservative, a solvent, and, optionally, an antioxidant.

3. The system of claim 1, further comprising:
    (f) about 0.001 to about 5% by weight of a preservative selected from sodium thiosulfate pentahydrate, benzyl alcohol, parabens, and mixtures thereof.

4. The system of claim 3, comprising:
    (a) about 5 to about 10% by weight potassium 2,5-dihydroxybenzenesulfonate;
    (b) about 65 to about 70% by weight white petrolatum, mineral oil, or mixtures thereof;
    (c) about 5% by weight steareth-2 (Brij 72), steareth-21 (Brij 721), or mixtures thereof;
    (d) about 0.1 to about 2% by weight stearyl alcohol, cetyl alcohol, or mixtures thereof;
    (e) about 0.05 to about 1% by weight acetic acid solution, sodium acetate, or mixtures thereof;
    (f) about 0.1 to about 1% by weight of benzyl alcohol, sodium thiosulfate pentahydrate, butyl paraben, or mixtures thereof; and
    water to 100%.

5. The system of claim 1, which is administered daily.

6. The system of claim 1, which is effective for topical treatment of one or more of: rosacea, acne, cancers of the skin, actinic keratosis, dermatitis, and psoriasis.

7. The system of claim 1, wherein the potassium 2,5-dihydroxybenzenesulfonate is suspended in the emulsion.

* * * * *